US011058705B2

(12) United States Patent
Joshi-Hangal et al.

(10) Patent No.: US 11,058,705 B2
(45) Date of Patent: *Jul. 13, 2021

(54) DRUG FORMULATIONS

(71) Applicant: Astex Pharmaceuticals, Inc., Pleasanton, CA (US)

(72) Inventors: Rajashree Joshi-Hangal, Pleasanton, CA (US); Chunlin Tang, Walnut Creek, CA (US); Sanjeev Redkar, San Ramon, CA (US); Harish Ravivarapu, Pleasanton, CA (US)

(73) Assignee: ASTEX PHARMACEUTICALS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/675,785

(22) Filed: Nov. 6, 2019

(65) Prior Publication Data
US 2020/0155588 A1 May 21, 2020

Related U.S. Application Data

(63) Continuation of application No. 15/879,802, filed on Jan. 25, 2018, now Pat. No. 10,517,886, which is a continuation of application No. 15/174,386, filed on Jun. 6, 2016, now Pat. No. 9,913,856, which is a continuation of application No. 14/241,635, filed as application No. PCT/US2012/052816 on Aug. 29, 2012, now Pat. No. 9,381,207.

(60) Provisional application No. 61/529,081, filed on Aug. 30, 2011.

(51) Int. Cl.
| | |
|---|---|
| *A01N 43/04* | (2006.01) |
| *A61K 31/70* | (2006.01) |
| *A61K 31/7084* | (2006.01) |
| *A61K 31/706* | (2006.01) |
| *A61K 31/7056* | (2006.01) |
| *A61K 31/7064* | (2006.01) |
| *A61K 31/7052* | (2006.01) |
| *A61K 9/00* | (2006.01) |
| *A61K 47/10* | (2017.01) |
| *A61K 47/20* | (2006.01) |
| *A61K 9/19* | (2006.01) |
| *A61K 31/708* | (2006.01) |

(52) U.S. Cl.
CPC ........ *A61K 31/7084* (2013.01); *A61K 9/0019* (2013.01); *A61K 9/19* (2013.01); *A61K 31/706* (2013.01); *A61K 31/708* (2013.01); *A61K 31/7052* (2013.01); *A61K 31/7056* (2013.01); *A61K 31/7064* (2013.01); *A61K 47/10* (2013.01); *A61K 47/20* (2013.01)

(58) Field of Classification Search
None
See application file for complete search history.

(56) References Cited

U.S. PATENT DOCUMENTS

| | | | |
|---|---|---|---|
| 3,133,858 A * | 5/1964 | Hartop, Jr. | .......... A61K 9/0019 514/271 |
| 6,905,669 B2 | 6/2005 | Dimartino | |
| 6,919,370 B2 | 7/2005 | Chen | |
| 6,982,253 B2 | 1/2006 | Joshi-Hangal et al. | |
| 6,998,391 B2 | 2/2006 | Lyons et al. | |
| 7,135,464 B2 | 11/2006 | Joshi-Hangal et al. | |
| 7,144,873 B2 | 12/2006 | Joshi-Hangal et al. | |
| 7,250,416 B2 | 7/2007 | Phiasivongsa et al. | |
| 7,276,228 B2 | 10/2007 | Dimartino | |
| 7,700,567 B2 * | 4/2010 | Phiasivongsa | ........ C12N 15/111 514/43 |
| 8,003,324 B2 | 8/2011 | Dudley, Jr. | |
| 8,461,123 B2 | 6/2013 | Phiasivongsa et al. | |
| 9,358,248 B2 | 6/2016 | Phiasivongsa et al. | |
| 9,381,207 B2 | 7/2016 | Joshi-Hangal et al. | |
| 9,480,698 B2 | 11/2016 | Phiasivongsa et al. | |
| 9,913,856 B2 | 3/2018 | Joshi-Hangal et al. | |
| 10,456,415 B2 | 10/2019 | Phiasivongsa et al. | |
| 10,517,886 B2 | 12/2019 | Joshi-Hangal et al. | |
| 10,519,190 B2 | 12/2019 | Joshi-Hangal et al. | |
| 2002/0114809 A1 | 8/2002 | Rubinfeld et al. | |
| 2003/0147813 A1 | 8/2003 | Lyons | |
| 2003/0229047 A1 | 12/2003 | Joshi-Hangal et al. | |
| 2004/0052864 A1 | 3/2004 | Rubinfeld et al. | |
| 2004/0109846 A1 | 6/2004 | Rubinfeld et al. | |
| 2004/0162263 A1 | 8/2004 | Sands et al. | |
| 2004/0224919 A1 | 11/2004 | Rubinfeld et al. | |

(Continued)

FOREIGN PATENT DOCUMENTS

| | | |
|---|---|---|
| CN | 101282986 A | 10/2008 |
| CN | 101361718 A | 2/2009 |

(Continued)

OTHER PUBLICATIONS

Vemula et al. International Journal of Pharmaceutical Sciences Review and Research (2010), vol. 5, pp. 41-51.*
Chuang, et al. S110, a 5-Aza-2'-deoxycytidine-containing dinucleotide, is an effective DNA methylation inhibitor in vivo and can reduce tumor growth. Molecular cancer therapeutics 9.5 (2010): 1443-1450.
Dacogen™ (Decitabine) for Injection.
Das Gupta, V. Effect of ethanol, glycerol, and propylene glycol on the stability of phenobarbital sodium. J Pharm Sci. Nov. 1984;73(11):1661-2.

(Continued)

*Primary Examiner* — Patrick T Lewis
(74) *Attorney, Agent, or Firm* — Wilson Sonsini Goodrich & Rosati

(57) ABSTRACT

The invention provides derivatives of decitabine with superior chemical stability and shelf life, with similar physiological activity. The derivatives are provided in a non-aqueous formulation, which further stabilizes the derivatives. Methods of treating one or more myelodysplastic syndromes, leukemia, or solid tumours using the formulations are described.

19 Claims, 4 Drawing Sheets

(56) References Cited

U.S. PATENT DOCUMENTS

| | | |
|---|---|---|
| 2005/0037992 A1 | 2/2005 | Lyons et al. |
| 2005/0059682 A1 | 3/2005 | Rubinfeld |
| 2005/0159375 A1 | 7/2005 | Srivastava et al. |
| 2005/0209186 A1 | 9/2005 | Lyons |
| 2006/0014949 A1 | 1/2006 | Redkar et al. |
| 2006/0063735 A1 | 3/2006 | Redkar et al. |
| 2006/0069060 A1 | 3/2006 | Redkar et al. |
| 2006/0074046 A1 | 4/2006 | Redkar et al. |
| 2006/0128653 A1 | 6/2006 | Tang et al. |
| 2006/0128654 A1 | 6/2006 | Tang et al. |
| 2006/0140947 A1 | 6/2006 | Lyons et al. |
| 2006/0205687 A1 | 9/2006 | Phiasivongsa et al. |
| 2007/0072796 A1 | 3/2007 | Phiasivongsa et al. |
| 2007/0105792 A1 | 5/2007 | Dimartino |
| 2007/0117776 A1 | 5/2007 | Lyons |
| 2007/0254835 A1 | 11/2007 | Lyons et al. |
| 2008/0108559 A1 | 5/2008 | Dimartino |
| 2010/0062992 A1 | 3/2010 | Redkar et al. |
| 2010/0215729 A1 | 8/2010 | Phiasivongsa et al. |
| 2013/0236536 A1 | 9/2013 | Phiasivongsa et al. |

FOREIGN PATENT DOCUMENTS

| | | |
|---|---|---|
| EP | 0251464 A2 | 1/1988 |
| WO | WO-02085400 A1 | 10/2002 |
| WO | WO-03065995 A2 | 8/2003 |
| WO | WO-03103687 A1 | 12/2003 |
| WO | WO-2006063111 A2 | 6/2006 |
| WO | WO-2006071491 A1 | 7/2006 |
| WO | WO-2006099132 A1 | 9/2006 |
| WO | WO-2007041071 A2 | 4/2007 |
| WO | WO-2013033176 A1 | 3/2013 |

OTHER PUBLICATIONS

European Office Action dated Apr. 14, 2015 for EP Application No. 12759857.1.
European Office Action dated Oct. 19, 2016 for EP Application No. 12759857.1.
European Serial No. 18177788.9 Extended Search Report dated Jan. 4, 2019.
International search report and written opinion dated Nov. 7, 2012 for PCT/US2012/052816.
Lin, K.S. et al. High-Performance Liquid Chromatographic Analysis of Chemical Stability of 5-Aza-2'-deoxycytidine. Journal of Pharmaceutical Sciences. 1981; 70(11): 1228-1232.
Liu, et al. Solubility of Rofecoxib in the Presence of Aqueous Solutions of Glycerol, Propylene Glycol, Ethanol, Span 20, Tween 80, and Sodium Lauryl Sulfate at 9298.15, 303.15, and 308.15) K, J. Chem. Eng. Data (2005), 50, 2061-2064.
Non-Final Office Action dated Feb. 21, 2019 in U.S. Appl. No. 15/879,802.
Notice of allowance dated Mar. 7, 2016 for U.S. Appl. No. 14/241,635.
Notice of allowance dated Nov. 23, 2015 for U.S. Appl. No. 14/241,635.
Notice of allowance dated Dec. 14, 2017 for U.S. Appl. No. 15/174,386.
Notice of Allowance dated Oct. 16, 2019 in U.S. Appl. No. 15/879,802.
Office action dated May 26, 2017 for U.S. Appl. No. 15/174,386.
Office action dated Jul. 30, 2015 for U.S. Appl. No. 14/241,635.
Vemula et al., "Solubility Enhancement Techniques" International Journal of Pharmaceutical Sciences Review and Research, (2010), vol. 5, pp. 41-51.
Yalkowsky, et al. "Solubilization by Cosolvents I: Organize Solutes in Propylene Glycol-Water Mixtures" Journal of Pharmaceutical Sciences (1985), vol. 74, pp. 416-421.

* cited by examiner

DRUG FORMULATIONS

RELATED APPLICATIONS

This application is a continuation of U.S. application Ser. No. 15/879,802 filed Jan. 25, 2018, which is a continuation of U.S. application Ser. No. 15/174,386, filed Jun. 6, 2016, now U.S. Pat. No. 9,913,856, which is a continuation of U.S. application Ser. No. 14/241,635, filed Jun. 12, 2014, now U.S. Pat. No. 9,381,207, which is a U.S. National Stage application under 35 U.S.C. § 371 of PCT Application No. PCT/US12/52816, filed Aug. 29, 2012, which claims the benefit under 35 U.S.C. § 119 of U.S. Provisional Patent Application 61/529,081, filed Aug. 30, 2011, the contents of each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Decitabine is currently being developed as a pharmaceutical for the treatment of chronic myelogenous leukemia (CML), myelodysplastic syndrome (MDS), non-small cell lung (NSCL) cancer, sickle-cell anemia, and acute myelogenous leukemia (AML). Decitabine possesses multiple pharmacological characteristics. Decitabine can be incorporated into DNA during the S phase of cell cycle, or can induce cell differentiation and exert haematological toxicity. Despite having a short physiological half-life, decitabine has an excellent tissue distribution.

Despite its proven antileukemic effects in CML, MDS, and AML, the potential application of decitabine has been hampered by delayed and prolonged myelosuppression. Lower doses of decitabine, given over a longer period of time, have minimized myelosuppression to manageable levels without compromising its ability to suppress cancer via its hypomethylation effect. At higher doses, the associated toxicity was prohibitive. However, treatment of haematologic and solid tumours at maximally tolerated doses of decitabine has been ineffective. The cause of myelosuppression is not clear. It is plausible that since decitabine is randomly and extensively incorporated into the DNA of S phase cells, including bone marrow cells that are involved in normal haematopoiesis, the severe DNA damage due to the instability of decitabine leads to necrosis. Since incorporation of decitabine is not restricted to only the CpG-rich sequences, the DNA can break, due to the instability of decitabine, and require repair at numerous sites outside of the CpG islands.

Decitabine and azacitidine are unstable in aqueous media and undergo hydrolytic degradation in aqueous media. The degradation is slowest at neutral pH.

Dinucleotide compounds derived from decitabine for the development of therapies for similar indications had been described in U.S. Pat. No. 7,700,567, which is incorporated by reference in its entirety.

SUMMARY OF THE INVENTION

In a first aspect of the present invention there is provided a formulation comprising: (a) a compound of the formula:

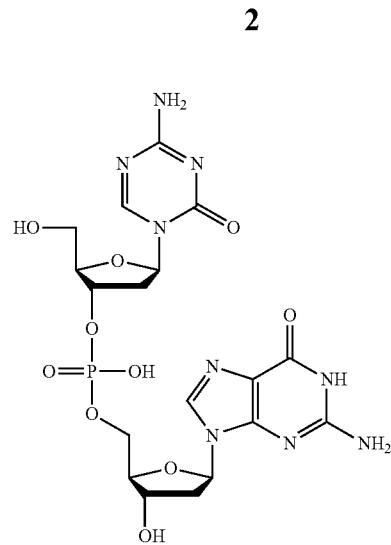

I-1 or a pharmaceutically-acceptable salt thereof; dissolved in (b) a substantially anhydrous solvent comprising about 45% to about 85% propylene glycol; about 5% to about 45% glycerin; and 0% to about 30% ethanol.

In some embodiments, said solvent comprises about 65% to about 70% propylene glycol; about 25% to about 30% glycerin, and 0% to about 10% ethanol.

It has been found that the use of a substantially anhydrous solvent in the formulations of the invention produces a dramatic increase in the solubility (about 130 to about 150 mg/mL for the compound of formula I-1). This improves subcutaneous administration, since such high concentrations lower the volumes of injection and increase the safety of the compound as less amounts of excipients are needed compared to lower concentrations of the same compound.

It has also been found that the use of substantially anhydrous solvents in the formulations of the invention exhibit increased shelf life stability (see Example 2 herein). For example, reconstituted dosage forms having a water content of 0.1% remain stable at 2-8° C. for at least 12 months.

Ethanol can be incorporated as a thinning agent or can be eliminated while retaining suitable handling/reconstitution characteristics.

In some embodiments, said solvent comprises about 65% propylene glycol; about 25% glycerin; and about 10% ethanol, for example being 65% propylene glycol; 25% glycerin; and 10% ethanol.

In some embodiments, said solvent comprises 65% to 70% propylene glycol and 25% to 30% glycerin, any balance being ethanol.

In some embodiments, said solvent comprises about 70% propylene glycol and about 30% glycerin, ethanol being absent.

In some embodiments, said solvent comprises: 45% to 85% propylene glycol; 5% to 45% glycerin; and 0% to 30% ethanol; or 65% to 70% propylene glycol; 25% to 30% glycerin, and 0% to 10% ethanol.

Non-limiting embodiments of a pharmaceutically-acceptable salt include any salt described herein. In some embodiments, said salt is a sodium salt. The compound can be present at a concentration of about 80 mg/mL to about 110 mg/mL, for example about 100 mg/mL.

In some embodiments, the formulation further comprises dimethyl sulfoxide (DMSO), optionally at a DMSO:compound ratio of about 2:about 1; about 1:about 1; about 0.5:about 1; about 0.3:about 1; or about 0.2-about 0.3:about 1.

In some embodiments, a formulation disclosed herein is suitable for administration by subcutaneous injection.

In another aspect, the invention provides a kit comprising: (a) a first vessel containing a compound or pharmaceutically-acceptable salt thereof as described herein; and (b) a second vessel containing a substantially anhydrous solvent comprising about 45% to about 85% propylene glycol; about 5% to about 45% glycerin; and 0% to about 30% ethanol.

In some embodiments, the compound in the kit of the invention is present in the form of a substantially anhydrous powder, for example a lyophilized powder. The compound can be present in the first vessel in an amount of about 80 mg to about 110 mg, for example about 100 mg. In some embodiments, the kit further comprises instructions for administration by subcutaneous injection.

In another aspect, the invention provides a process for preparing a pharmaceutical composition, the process comprising dissolving a compound as described herein in a substantially anhydrous solvent. Non-limiting examples of such a substantially anhydrous solvent include any substantially anhydrous solvent described herein.

In some embodiments, the process further comprises the steps of: dissolving said compound in DMSO to produce a solution of said compound in DMSO; and lyophilizing said solution to provide said compound as a substantially anhydrous powder.

In another aspect, the invention provides a process for producing a compound of the formula:

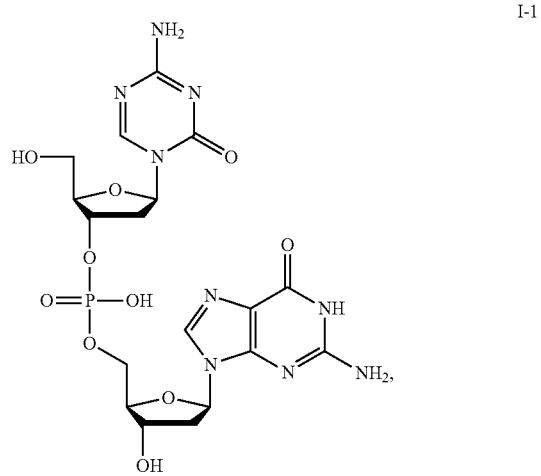

I-1 or a pharmaceutically-acceptable salt thereof, in the form of a substantially anhydrous powder, the process comprising dissolving said compound or salt thereof in DMSO to produce a solution in DMSO, and then lyophilizing said solution to provide said compound or salt thereof as a substantially anhydrous powder. Said substantially anhydrous powder can comprise DMSO, for example, in an amount of up to about 2000 mg/g; up to about 1000 mg/g; up to about 600 mg/g; up to about 500 mg/g; up to about 400 mg/g; up to about 300 mg/g or about 200-about 300 mg/g of said compound of formula I-1. In some embodiments, the powder comprises up to about 200%, up to about 100%, up to about 60%, up to about 50%, up to about 40%, up to about 30%, or about 20%-about 30% w/w DMSO/compound of formula I-1.

In another aspect, the invention provides a substantially anhydrous powder consisting essentially of a compound of the formula:

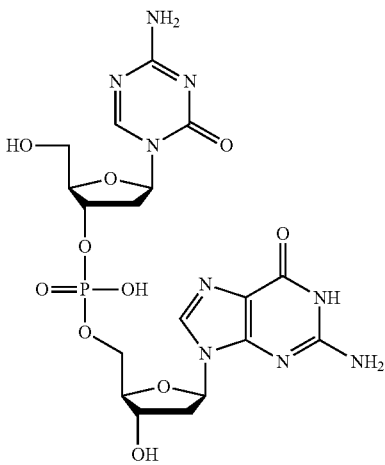

I-1 or a pharmaceutically-acceptable salt thereof, and DMSO, the DMSO being present in an amount of up to about 200% w/w DMSO/compound of formula I-1. In one embodiment, the DMSO is present in an amount of up to about 100%, up to about 60%, up to about 50%, up to about 40%, or up to about 30% w/w DMSO/compound of formula I-1. In some embodiments, the DMSO is present in an amount of about 20-about 30% w/w DMSO/compound of formula I-1. In some embodiments, the salt of the powder is a sodium salt.

In another aspect, the invention provides a pharmaceutical composition obtainable by the processes of the invention.

In another aspect, the invention provides a method for treating a cancer, myelodysplastic syndrome, leukemia or solid tumour comprising administering the formulation, kit, powder or composition of the invention to a subject in need or want thereof.

In another aspect, the invention provides the formulation, kit, powder or composition of the invention for use in a method of treating a cancer, myelodysplastic syndrome, leukemia or solid tumour, said method comprising administering said formulation, kit, powder or composition of the invention to a subject.

In another aspect, the invention provides the use of the formulation, kit, powder or composition of the invention for the manufacture of a medicament for use in a method of treating a cancer, myelodysplastic syndrome, leukemia or solid tumour, said method comprising administering said formulation, kit, powder or composition of the invention to a subject.

The methods, formulations, compositions, kits, powders or uses of the invention find application in the treatment of a wide variety of diseases that are sensitive to the treatment with decitabine, including those described herein as non-limiting examples.

In some embodiments, the administration is subcutaneous administration.

Any compound described herein is suitable for use in any formulation, powder, or kit described herein.

DETAILED DESCRIPTION OF THE INVENTION

Figure 1:
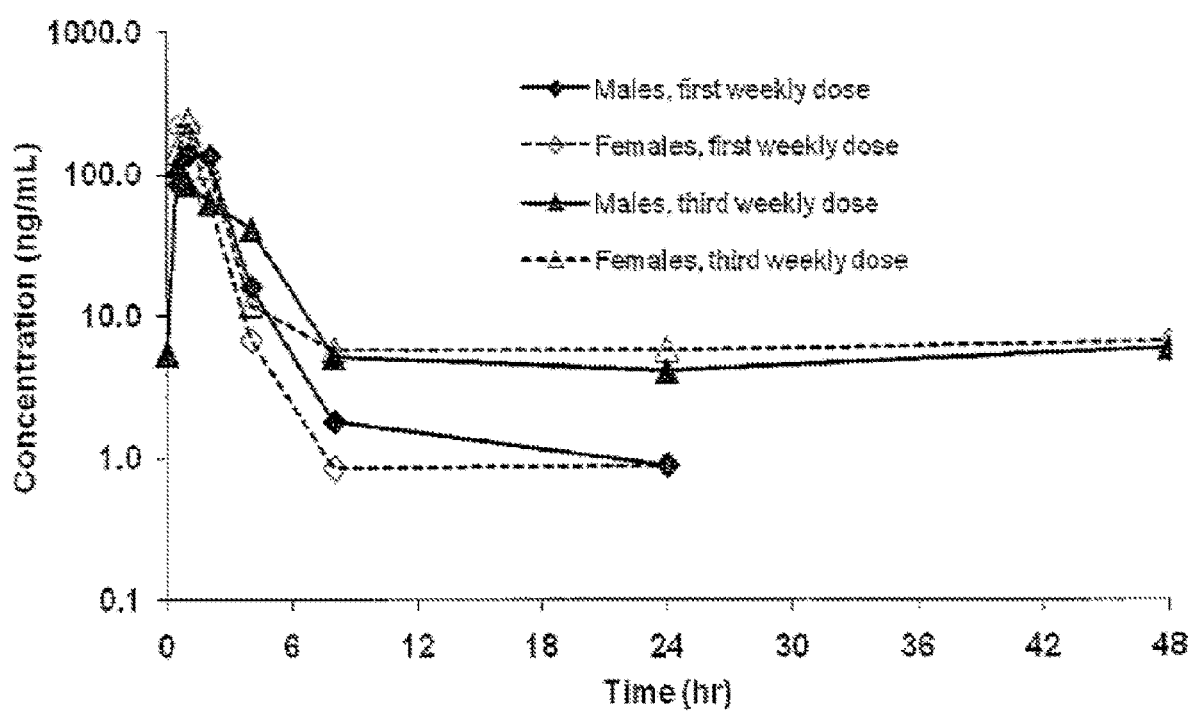
FIG. 1 illustrates the mean plasma concentrations of the compound I-1 in male and female cynomolgus monkeys given weekly subcutaneous doses of compound I-1 in a pharmacokinetic study.

In current clinical treatment with decitabine, to minimize decomposition, decitabine is supplied as a lyophilized powder and reconstituted pre-administration in a cold solution containing at least 40% water (v/v), such as water for injection (WFI). This method requires refrigeration of decitabine in solution, but such storage is inconvenient and economically less desirable than storage at ambient temperatures. Due to rapid decomposition of decitabine in aqueous solution, the reconstituted decitabine solution can be infused only within hours of reconstitution. Refrigeration after reconstitution is undesirable because infusion of cold fluid can cause discomfort, pain, and subsequently, non-compliance in the subject. The inventions described herein solve these problems by providing formulations of decitabine derivatives in formulations that resist chemical decomposition and provide greater convenience and versatility in a therapeutic regimen.

The inventions describe formulations of compounds derived from decitabine with improved chemical stability and greater ability to deliver pharmaceutically-active agent to a subject in need or want thereof. The compounds incorporate a 5-aza-cytosine group, optionally in the form of a 5-aza-2'-deoxycytidine group (decitabine) or a 5-aza-cytidine group. The compounds also incorporate a guanine group, optionally in the form of a 2'-deoxyguanidine group or a guanidine group. The 5-aza-cytosine group and the guanine group are linked by one of a variety of phosphorus-containing linkers.

A phosphorus-containing linker is a moiety comprising a phosphorus atom. In some embodiments, the number of phosphorus atoms in the phosphorus-containing linker is 1. Non-limiting examples of phosphorus-containing linkers include groups comprising a phosphodiester, a phosphorothioate diester, a boranophosphate diester, and a methylphosphonate diester.

The compounds are provided in formulations that preserve the efficacy of the compounds by providing media wherein the compounds exhibit good chemical stability.

Compounds

In some embodiments, the invention provides a formulation comprising: a) a compound of Formula I or a pharmaceutically-acceptable salt thereof:

(5-azacytosine group)-L-(guanine group)        (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient.

In some embodiments, the invention provides a formulation comprising: a) a compound of the formula:

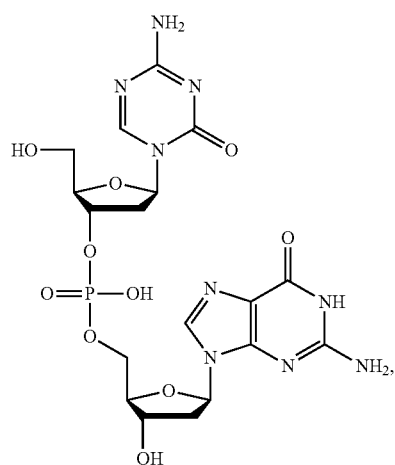

or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

In some embodiments, the invention provides a method of treating one or more myelodysplastic syndromes, leukemia, or solid tumours, the method comprising administering a formulation to a subject in need or want thereof, the formulation comprising: a) a therapeutically-effective amount of a compound of Formula I or a pharmaceutically-acceptable salt thereof:

(5-azacytosine group)-L-(guanine group)        (I), wherein L is a phosphorus-containing linker wherein the number of phosphorus atoms in L is 1; b) a solvent comprising: about 45% to about 85% propylene glycol; about 5% to about 45% glycerin; and 0% to about 30% ethanol; and c) optionally, a pharmaceutically-acceptable excipient.

In some embodiments, the invention provides a method of treating one or more myelodysplastic syndromes, leukemia, or solid tumours, the method comprising administering a formulation to a subject in need or want thereof, the formulation comprising: a) a therapeutically-effective amount of a compound of the formula:

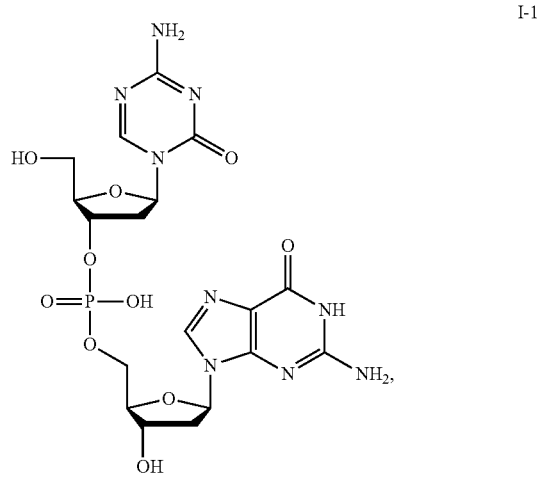

or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

In some embodiments, the invention provides formulations comprising a compound of Formula I or a pharmaceutically-acceptable salt thereof:

(5-azacytosine group)-L-(guanine group)　　　(I), wherein L is a phosphorus-containing linker wherein the number of phosphorus atoms in L is 1.

L is a group suitable for linking the 5-azacytosine group with the guanine group. In some embodiments, L comprises a carbohydrate. In some embodiments, L comprises more than one carbohydrate. In some embodiments, L comprises two carbohydrates. When L comprises more than one carbohydrate, the carbohydrates can be the same or different. A carbohydrate can be a monosaccharide in the closed ring form, such as a pyranose or furanose form. A carbohydrate can be substituted at any position or deoxygenated at any position that would be oxygenated in a naturally-occurring form of the carbohydrate. In some embodiments, the carbohydrate is ribose. In some embodiments, the carbohydrate is 2-deoxyribose. The ribose or 2-deoxyribose can be substituted at any position.

The phosphate atom of L can be present in any naturally-occurring or synthetic functional group containing a phosphorus atom. Non-limiting examples of such functional groups include phosphodiesters, phosphorothioate diesters, boranophosphate diesters, and methylphosphonate diesters.

In some embodiments, L comprises Formula II. In some embodiments, L is Formula II.

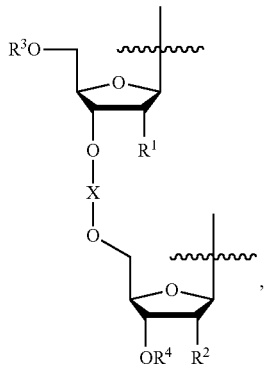

(II)

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, a carbonate, or a carbamate; $R^4$ is H, or $R^4$ together with the oxygen atom to which $R^4$ is bound forms an ether, an ester, a carbonate, or a carbamate; and X together with the oxygen atoms to which X is bound forms a phosphodiester, a phosphorothioate diester, a boranophosphate diester, or a methylphosphonate diester.

The 5-azacytosine group can be linked to either end of L, and the guanine group can be linked to the other end of L as long as the compound contains one 5-azacytosine group and one guanine group. Constitutional isomers can thus be prepared by exchanging the connectivity of the 5-azacytosine group and the guanine group.

$R^1$ and $R^2$ can be the same or different. In some embodiments, $R^1$ and $R^2$ are independently H, OH, OMe, OEt, OPh, $OCH_2CH_2OMe$, $OCH_2CH_2OEt$, $OCH_2CH_2OBn$, OBn, OAc, OBz, OCOOMe, OCOOEt, OCOOBn, $OCONH_2$, $OCONMe_2$, $OCONEt_2$, $OCONBn_2$, OCONHMe, OCONHEt, OCONHBn, F, Cl, Br, or I. In some embodiments, $R^1$ and $R^2$ are independently H, OH, OMe, OEt, $OCH_2CH_2OMe$, OBn, or F. In some embodiments, $R^1$ and $R^2$ are independently H or OH. In some embodiments, $R^1$ and $R^2$ are H. In some embodiments, $R^1$ and $R^2$ are OH.

$R^3$ and $R^4$ can be the same or different.

In some embodiments, $R^3$ is H, or $R^3$ together with the oxygen atom to which $R^3$ is bound forms OH, OMe, OEt, OPh, $OCH_2CH_2OMe$, $OCH_2CH_2OEt$, $OCH_2CH_2OBn$, OBn, OAc, OBz, OCOOMe, OCOOEt, OCOOBn, $OCONH_2$, $OCONMe_2$, $OCONEt_2$, $OCONBn_2$, OCONHMe, OCONHEt, or OCONHBn. In some embodiments, $R^3$ is H, or $R^3$ together with the oxygen atom to which $R^3$ is bound forms OH, OMe, OEt, $OCH_2CH_2OMe$, or OBn. In some embodiments, $R^3$ is H.

In some embodiments, $R^4$ is H, or $R^4$ together with the oxygen atom to which $R^4$ is bound forms OH, OMe, OEt, OPh, $OCH_2CH_2OMe$, $OCH_2CH_2OEt$, $OCH_2CH_2OBn$, OBn, OAc, OBz, OCOOMe, OCOOEt, OCOOBn, $OCONH_2$, $OCONMe_2$, $OCONEt_2$, $OCONBn_2$, OCONHMe, OCONHEt, or OCONHBn. In some embodiments, $R^4$ is H, or $R^4$ together with the oxygen atom to which $R^4$ is bound forms OH, OMe, OEt, $OCH_2CH_2OMe$, or OBn. In some embodiments, $R^4$ is H.

In some embodiments, X is P(O)OH, P(O)SH, P($\rightarrow$O)$BH_3^-$, or P(O)Me. In some embodiments, X is P(O)OH. In some embodiments, X together with the oxygen atoms to which X is bound forms a phosphodiester.

Non-limiting examples of alkyl include straight, branched, and cyclic alkyl groups. Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight or branched alkyl groups.

A halo-alkyl group can be any alkyl group substituted with any number of halogen atoms, for example, fluorine, chlorine, bromine, and iodine atoms.

An alkoxy group can be, for example, an oxygen atom substituted with any alkyl group. An ether or an ether group comprises an alkoxy group. Non-limiting examples of alkoxy groups include methoxy, ethoxy, propoxy, isopropoxy, and isobutoxy.

An alkoxyalkoxy group can be, for example, an alkoxy group substituted at any position with any alkoxy group. Non-limiting examples of alkoxyalkoxy groups include methoxyethoxy, ethyoxyethoxy, ethoxyethoxyethoxy, groups derived from any order of glyme, and groups derived from polyethylene glycol.

An aryl group can be heterocyclic or non-heterocyclic. An aryl group can be monocyclic or polycyclic. An aryl group can be substituted, for example, with any number of hydrocarbyl groups, alkyl groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon. A heterocycle can be substituted, for example, with any number of alkyl groups and halogen atoms. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group.

A carbonate group can be an oxygen atom substituted with hydrocarbyloxycarbonyl, alkoxycarbonyl, aryloxycarbonyl, or arylalkoxycarbonyl.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Any functional group of a compound described herein can be optionally capped with a capping group. For examples of capping groups, see GREENE'S PROTECTIVE GROUPS IN ORGANIC SYNTHESIS, 4th Ed. (Wiley 2006) (1980) and PROTECTING GROUPS, 3d Ed. (Thieme 2005) (1994), each of which is incorporated by reference in its entirety.

Non-limiting examples of suitable capping groups for a hydroxyl group include alkyl, haloalkyl, aryl, aralkyl, carbonate, carbamate, and acyl groups.

Non-limiting examples of suitable capping groups for nitrogen-functionalities include alkyl, aryl, aralkyl, an acyl group, an alkoxycarbonyl group, an aryloxycarbonyl group, and an aminocarbonyl group. A capping group together with the nitrogen atom to which the capping group is bound can form, for example, an amide, a carbamate, a urethane, a heterocycle, or an amine. Two capping groups bound to the same nitrogen atom can form together with the nitrogen atom a heterocycle.

The invention provides pharmaceutically-acceptable salts of any compound described herein. Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt. In some embodiments, a pharmaceutically-acceptable salt is an ammonium salt.

Acid addition salts can arise from the addition of an acid to a compound described herein. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

Non-limiting examples of compounds of Formula I include:

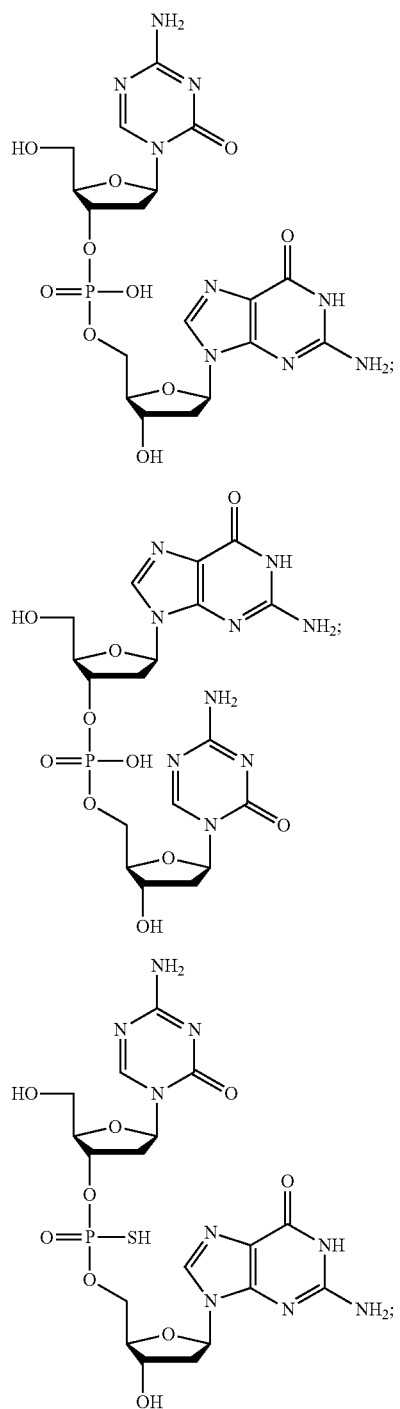

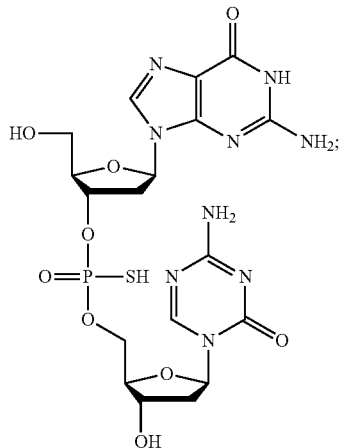

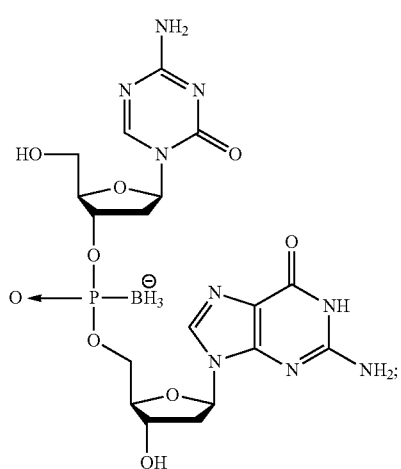

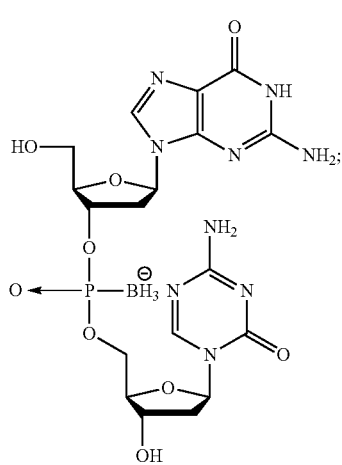

I-7
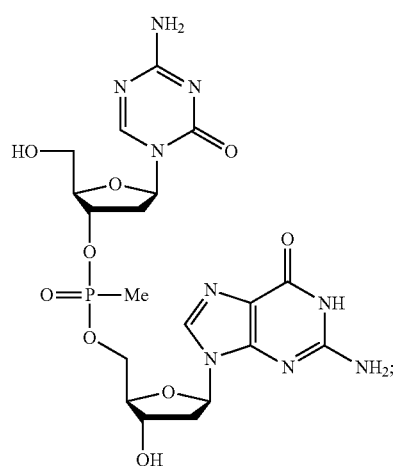
I-8
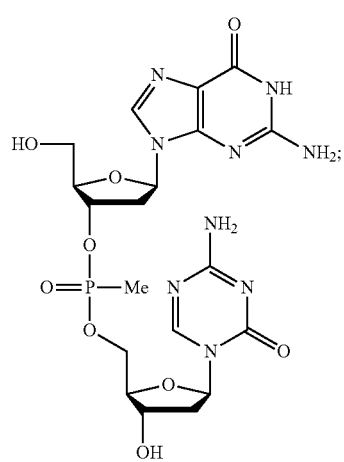
I-9
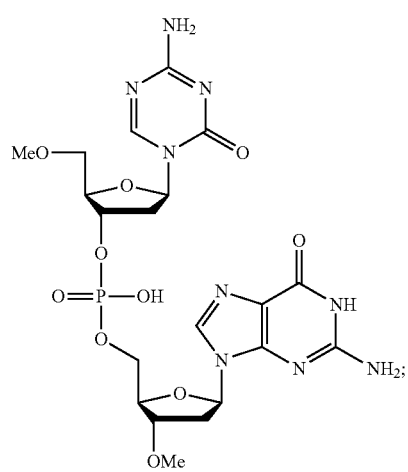
I-10
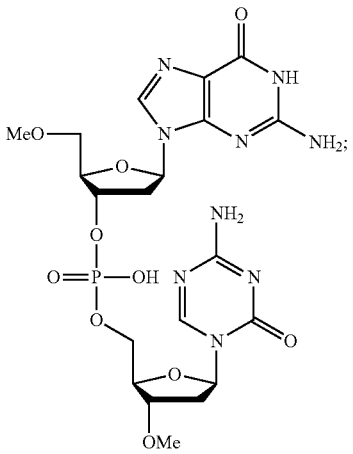
I-11
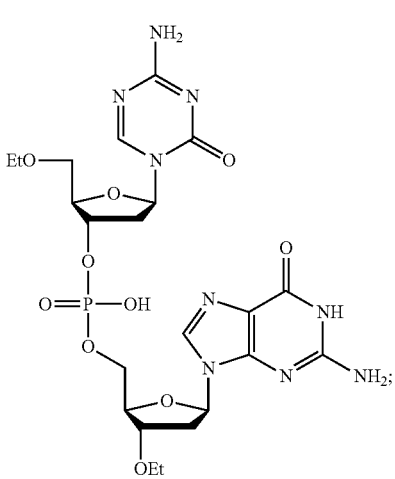
I-12
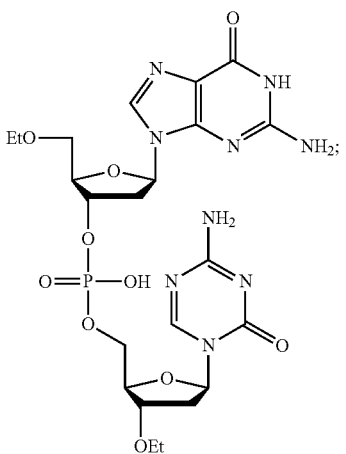

I-13
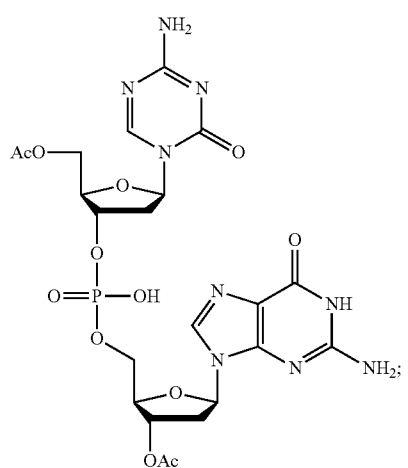
I-14
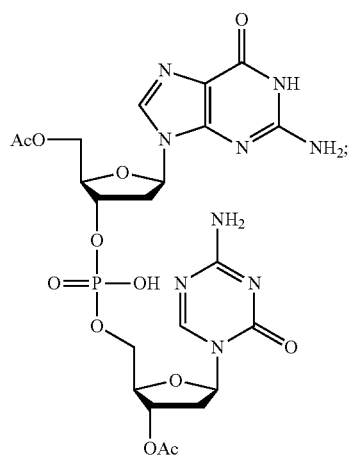
I-15
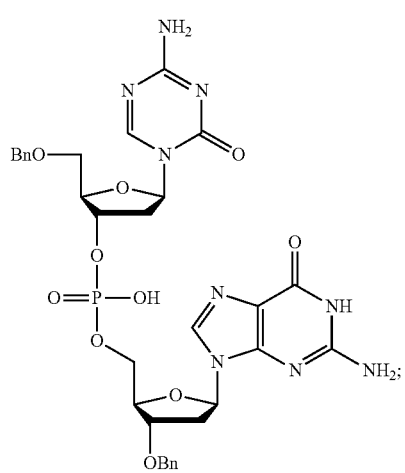
I-16
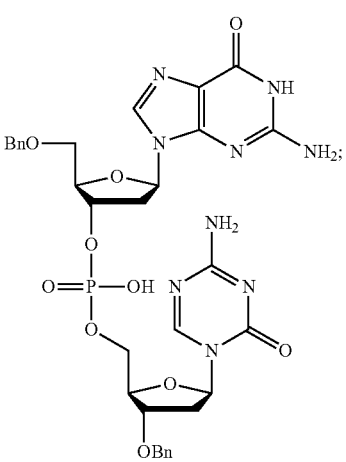
I-17
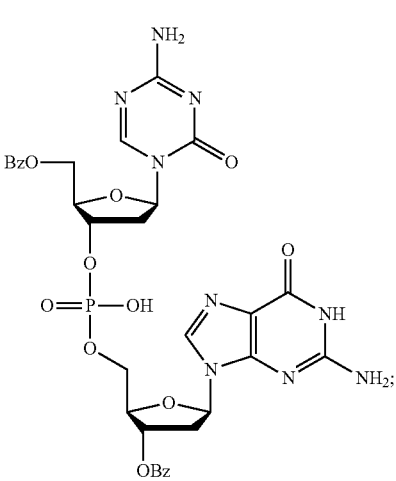
I-18
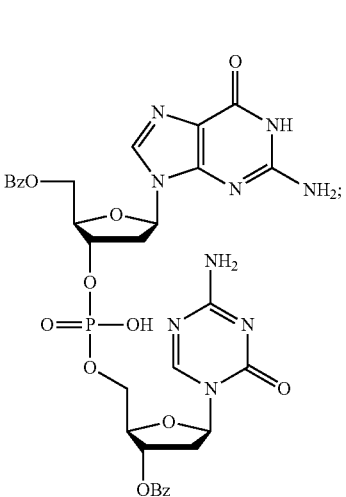

I-19
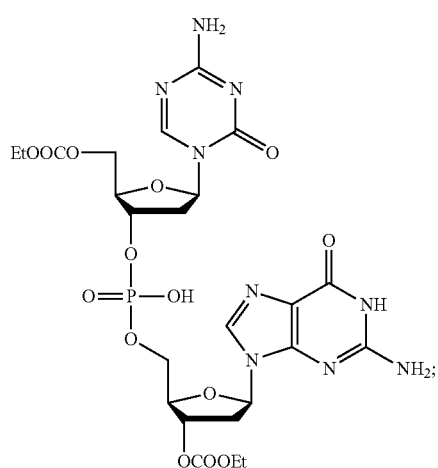
I-20
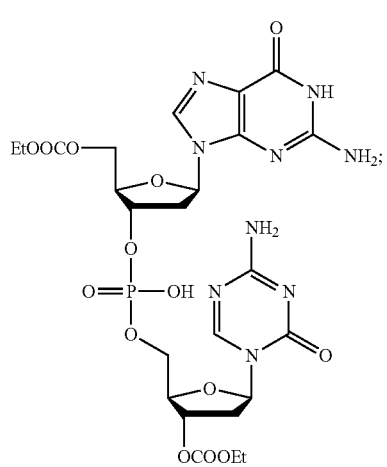
I-21
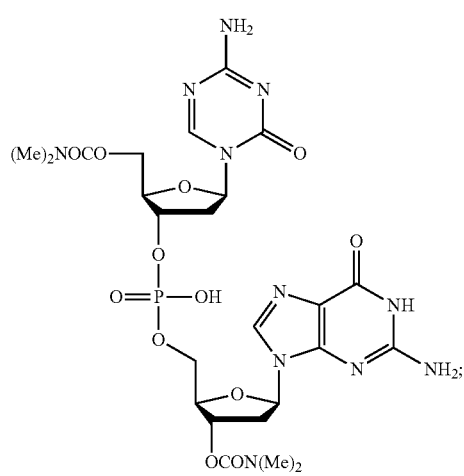
I-22
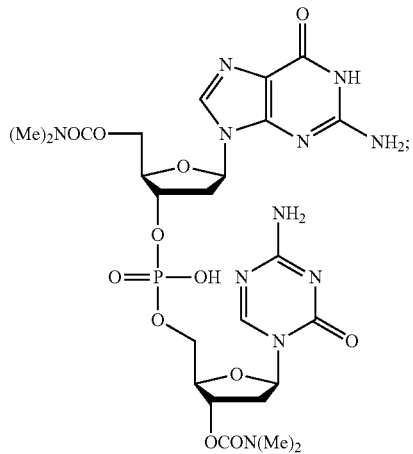
I-23
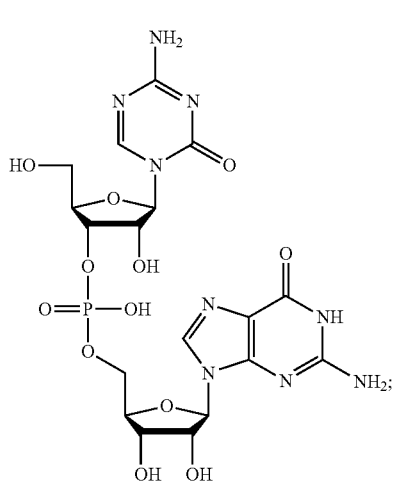
I-24
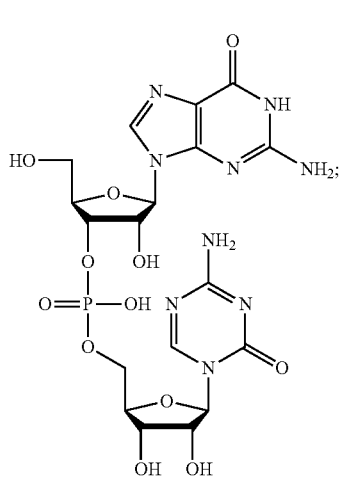

I-25
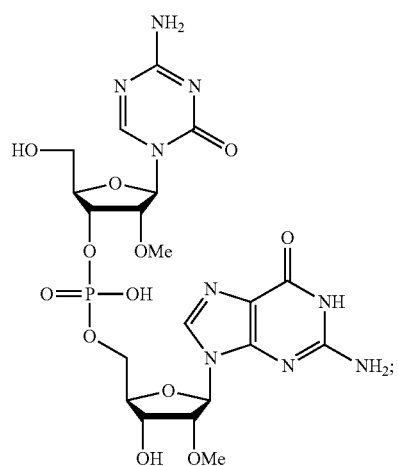
I-26
I-27
I-28
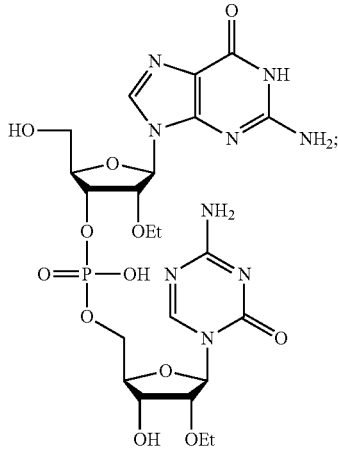
I-29
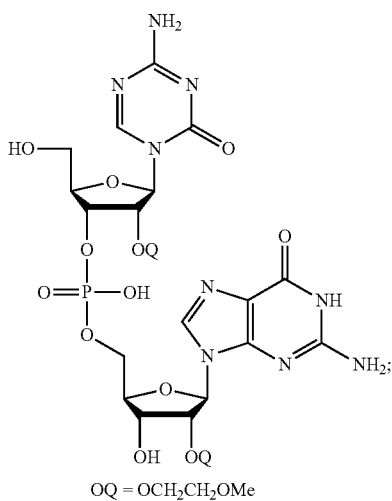
OQ = OCH$_2$CH$_2$OMe
I-30
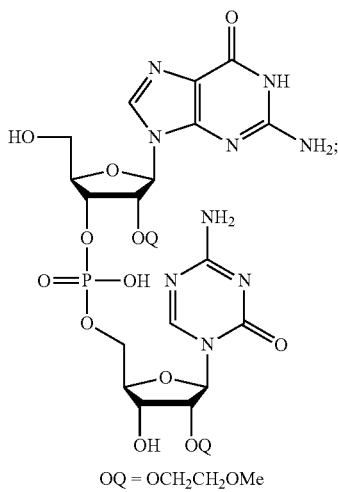
OQ = OCH$_2$CH$_2$OMe I-31
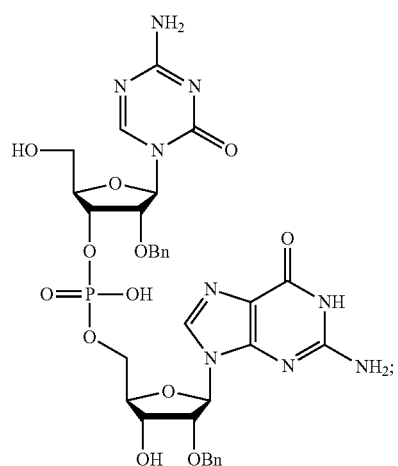
I-34
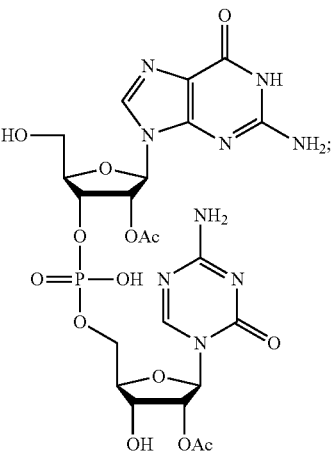
I-32
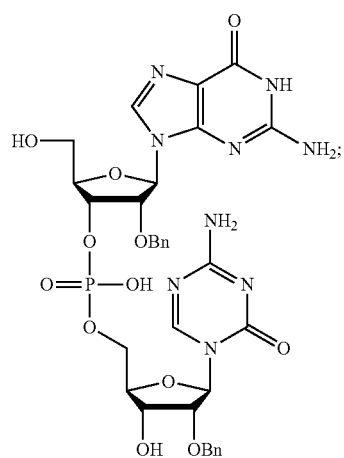
I-35
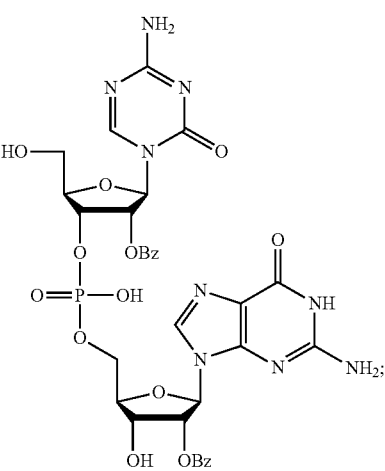
I-33
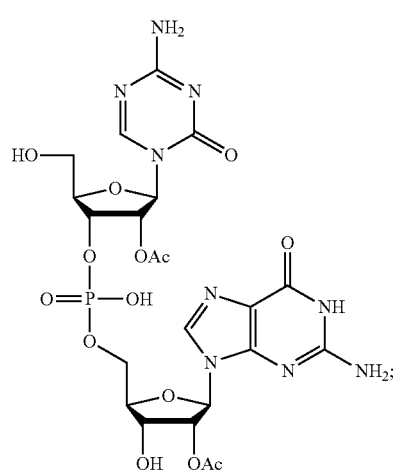
I-36

I-37
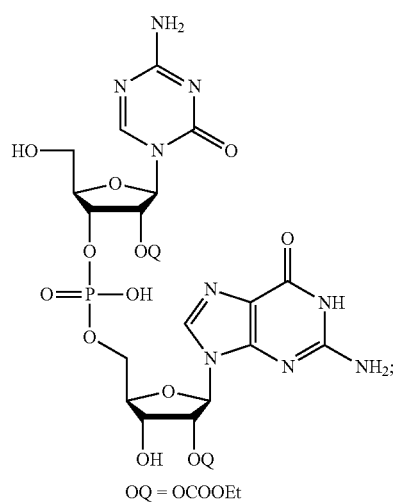
OQ = OCOOEt
I-38
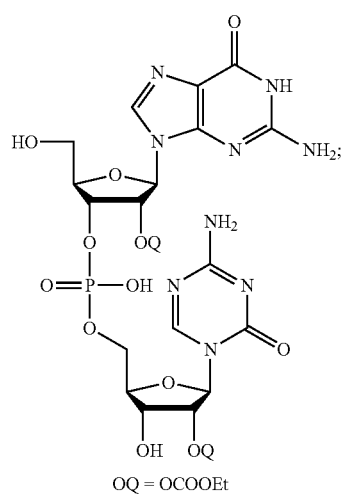
OQ = OCOOEt
I-39
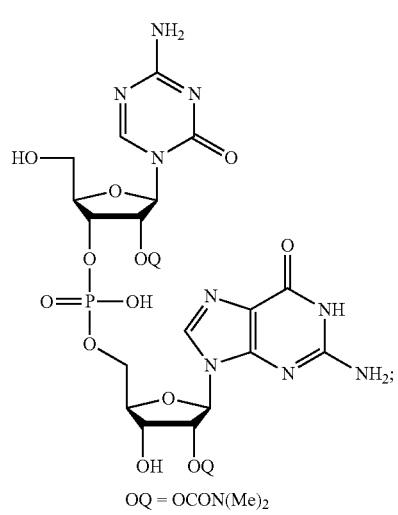
OQ = OCON(Me)₂
I-40
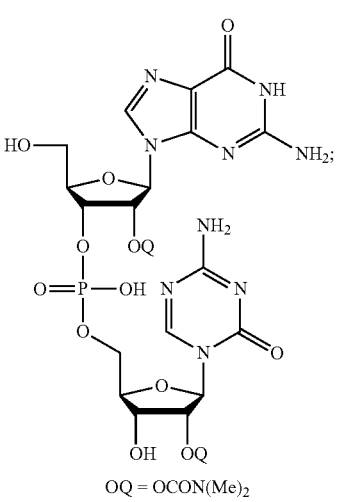
OQ = OCON(Me)₂
I-41
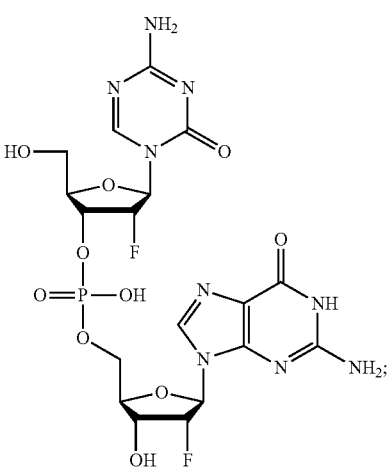
I-42
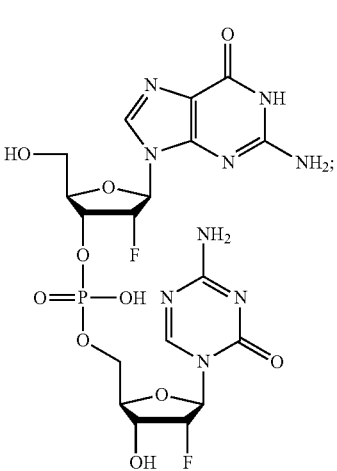

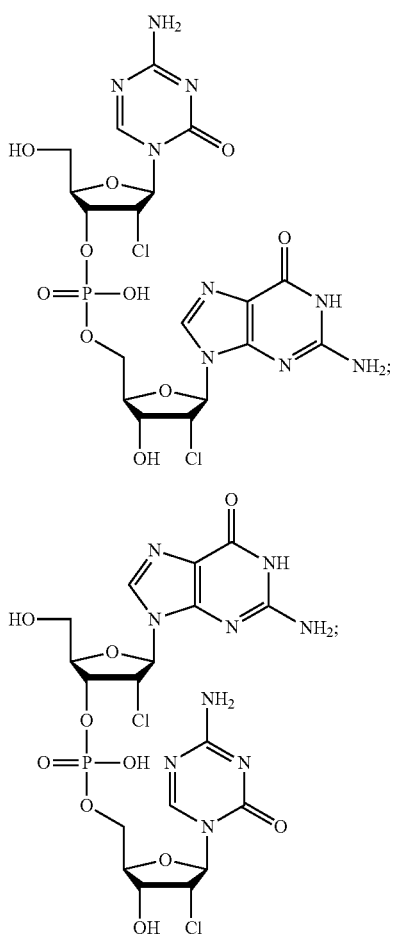

and pharmaceutically-acceptable salts of any of the foregoing.

The compounds described herein can be synthesized by methods known in the art, for example, solution phase or solid phase synthesis. For descriptions of the synthesis of compounds of the invention, and for a description of the mechanism of action of compounds of the invention, see U.S. Pat. No. 7,700,567, which is incorporated by reference herein in its entirety.

Formulations of the Invention.

Formulations described herein provide pharmaceutically-useful compositions comprising any compound described herein in a form with high solubility, low injection volumes, and good chemical stability and shelf-life. These properties provide formulations that retain a high percentage of the initial efficacy and deliver a therapeutically-effective amount of the compound even after storage at or below room temperature for extended times. In some embodiments, the invention provides a formulation comprising: a compound of Formula I or a pharmaceutically-acceptable salt thereof:

(5-azacytosine group)-L-(guanine group)　　(I), wherein L is a phosphorus-containing linker wherein the number of phosphorus atoms in L is 1. In some embodiments, the invention provides a formulation comprising: a) a compound of Formula I or a pharmaceutically-acceptable salt thereof:

(5-azacytosine group)-L-(guanine group)　　(I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient. Non-limiting examples of compounds suitable for use in formulations of the invention include compounds of Formula I wherein L is of Formula II. Non-limiting examples of compounds suitable for use in formulations of the invention include compounds I-(1-44).

Formulations can be solutions or suspensions of a compound in a solvent or a mixture of solvents. Non-limiting examples of suitable solvents include propylene glycol, glycerin, ethanol, and any combination of the foregoing. The formulations can be prepared as non-aqueous formulations. The formulations can be anhydrous or substantially anhydrous.

A mixture of solvents can contain a percentage of propylene glycol on either a mass or a volume basis. In some embodiments, the percentage of propylene glycol can be at least 10%, at least 20%, at least 30%, at least 40%, at least 50%, at least about 10%, at least about 20%, at least about 30%, at least about 40%, or at least about 50%. In some embodiments, the percentage of propylene glycol can be at most 90%, at most 80%, at most 70%, at most 60%, at most about 90%, at most about 80%, at most about 70%, or at most about 60%. In some embodiments, the percentage of propylene glycol can be 30% to 90%, 45% to 85%, 55% to 75%, 60% to 70%, about 30% to about 90%, about 45% to about 85%, about 55% to about 75%, or about 60% to about 70%. In some embodiments, the percentage of propylene glycol can be 30%, 35%, 40%, 45%, 50%, 55%, 60%, 65%, 70%, 75%, 80%, 85%, 90%, about 30%, about 35%, about 40%, about 45%, about 50%, about 55%, about 60%, about 65%, about 70%, about 75%, about 80%, about 85%, or about 90%.

A mixture of solvents can contain a percentage of glycerin on either a mass or a volume basis. In some embodiments, the percentage of glycerin can be at least 5%, at least 10%, at least 15%, at least 25%, at least 30%, at least about 5%, at least about 10%, at least about 15%, at least about 25%, or at least about 30%. In some embodiments, the percentage of glycerin can be at most 70%, at most 60%, at most 50%, at most 40%, at most 30%, at most about 70%, at most about 60%, at most about 50%, at most about 40%, or at most about 30%. In some embodiments, the percentage of glycerin can be 0% to 50%, 5% to 45%, 15% to 35%, 20% to 30%, 0% to about 50%, about 5% to about 45%, about 15% to about 35%, or about 20% to about 30%. In some embodiments, the percentage of glycerin can be 0%, 5%, 10%, 15%, 20%, 25%, 30%, 35%, 40%, 45%, 50%, about 5%, about 10%, about 15%, about 20%, about 25%, about 30%, about 35%, about 40%, about 45%, or about 50%.

A mixture of solvents can contain a percentage of ethanol on either a mass or a volume basis. In some embodiments, the percentage of ethanol can be at least 1%, at least 3%, at least 5%, at least 10%, at least 15%, at least about 1%, at least about 3%, at least about 5%, at least about 10%, or at least about 15%. In some embodiments, the percentage of ethanol can be at most 30%, at most 25%, at most 20%, at most 15%, at most 10%, at most about 30%, at most about 25%, at most about 20%, at most about 15%, or at most about 10%. In some embodiments, the percentage of ethanol can be 0% to 30%, 0% to 25%, 0% to 20%, 5% to 15%, 0% to about 30%, 0% to about 25%, 0% to about 20%, or about 5% to about 15%. In some embodiments, the percentage of ethanol can be 0%, 1%, 2%, 3%, 4%, 5%, 6%, 7%, 8%, 9%, 10%, 11%, 12%, 13%, 14%, 15%, about 1%, about 2%, about 3%, about 4%, about 5%, about 6%, about 7%, about 8%, about 9%, about 10%, about 11%, about 12%, about 13%, about 14%, or about 15%.

In some embodiments, a solvent or a mixture of solvents comprises 45% to 85% propylene glycol, 5% to 45% glycerin, and 0% to 30% ethanol. In some embodiments, a solvent or a mixture of solvents comprises about 45% to about 85% propylene glycol, about 5% to about 45% glycerin, and 0% to about 30% ethanol. In some embodiments, a solvent or a mixture of solvents consists essentially of 45% to 85% propylene glycol, 5% to 45% glycerin, and 0% to 30% ethanol. In some embodiments, a solvent or a mixture of solvents consists essentially of about 45% to about 85% propylene glycol, about 5% to about 45% glycerin, and 0% to about 30% ethanol. In some embodiments, a solvent or a mixture of solvents is 45% to 85% propylene glycol, 5% to 45% glycerin, and 0% to 30% ethanol. In some embodiments, a solvent or a mixture of solvents is about 45% to about 85% propylene glycol, about 5% to about 45% glycerin, and 0% to about 30% ethanol.

In some embodiments, a solvent or a mixture of solvents comprises 55% to 75% propylene glycol, 15% to 35% glycerin, and 0% to 20% ethanol. In some embodiments, a solvent or a mixture of solvents comprises about 55% to about 75% propylene glycol, about 15% to about 35% glycerin, and 0% to about 20% ethanol. In some embodiments, a solvent or a mixture of solvents consists essentially of 55% to 75% propylene glycol, 15% to 35% glycerin, and 0% to 20% ethanol. In some embodiments, a solvent or a mixture of solvents consists essentially of about 55% to about 75% propylene glycol, about 15% to about 35% glycerin, and 0% to about 20% ethanol. In some embodiments, a solvent or a mixture of solvents is 55% to 75% propylene glycol, 15% to 35% glycerin, and 0% to 20% ethanol. In some embodiments, a solvent or a mixture of solvents is about 55% to about 75% propylene glycol, about 15% to about 35% glycerin, and 0% to about 20% ethanol.

In some embodiments, a solvent or a mixture of solvents comprises 60% to 70% propylene glycol; 20% to 30% glycerin; and 5% to 15% ethanol. In some embodiments, a solvent or a mixture of solvents comprises about 60% to about 70% propylene glycol; about 20% to about 30% glycerin; and about 5% to about 15% ethanol. In some embodiments, a solvent or a mixture of solvents consists essentially of 60% to 70% propylene glycol; 20% to 30% glycerin; and 5% to 15% ethanol. In some embodiments, a solvent or a mixture of solvents consists essentially of about 60% to about 70% propylene glycol; about 20% to about 30% glycerin; and about 5% to about 15% ethanol. In some embodiments, a solvent or a mixture of solvents is 60% to 70% propylene glycol; 20% to 30% glycerin; and 5% to 15% ethanol. In some embodiments, a solvent or a mixture of solvents is about 60% to about 70% propylene glycol; about 20% to about 30% glycerin; and about 5% to about 15% ethanol.

In some embodiments, a solvent or a mixture of solvents comprises 65% propylene glycol; 25% glycerin; and 10% ethanol. In some embodiments, a solvent or a mixture of solvents comprises about 65% propylene glycol; about 25% glycerin; and about 10% ethanol. In some embodiments, a solvent or a mixture of solvents consists essentially of 65% propylene glycol; 25% glycerin; and 10% ethanol. In some embodiments, a solvent or a mixture of solvents consists essentially of about 65% propylene glycol; about 25% glycerin; and about 10% ethanol. In some embodiments, a solvent or a mixture of solvents is 65% propylene glycol; 25% glycerin; and 10% ethanol. In some embodiments, a solvent or a mixture of solvents is about 65% propylene glycol; about 25% glycerin; and about 10% ethanol.

A formulation can be prepared, stored, transported, and handled in anhydrous or substantially-anhydrous form. A solvent can be dried prior to preparing a formulation, and a compound can be dried, for example, by lyophilization. A drying agent, or desiccant, can be used during preparation, storage, transportation, or handling to regulate water content. Non-limiting examples of drying agents include silica gel, calcium sulfate, calcium chloride, calcium phosphate, sodium chloride, sodium bicarbonate, sodium sulfate, sodium phosphate, montmorillonite, molecular sieves (beads or powdered), alumina, titania, zirconia, and sodium pyrophosphate. A drying agent can contact a formulation directly, be inserted into the formulation in the form of a packet with a permeable membrane, or be stored with the formulation in a sealed environment, such as a dessicator, such that the drying agent and the formulation are simultaneously exposed to the same controlled atmosphere. A drying agent can be removed from a formulation, for example, by filtration or cannulation. Additionally, a formulation can be stored in a sealed container within a controlled atmosphere consisting essentially of, or enriched in, nitrogen or argon.

Anhydrous or substantially-anhydrous conditions benefit the shelf-life of a formulation disclosed herein at both ambient and reduced temperatures. This benefit reduces the costs associated with the storage, transportation, and spoilage of a formulation, increases the convenience of storage and handling, and avoids the need to administer cold formulations, thereby improving subject tolerance and compliance to a regimen of a formulation of the invention.

A formulation can further include a pharmaceutically-acceptable excipient. Non-limiting examples of excipients include mannitol, sorbitol, lactose, dextrose, and cyclodextrins. Excipients can be added to modulate the density, rheology, uniformity, and viscosity of the formulation.

A formulation can include acidic or basic excipients to modulate the acidity or basicity of the formulation. Non limiting examples of acids suitable to increase the acidity of a formulation include hydrochloric acid, hydrobromic acid, hydroiodic acid, sulfuric acid, phosphoric acid, nitric acid, ascorbic acid, citric acid, tartaric acid, lactic acid, oxalic acid, formic acid, benzenesulphonic acid, benzoic acid, maleic acid, glutamic acid, succinic acid, aspartic acid, diatrizoic acid, and acetic acid. Non limiting examples of bases suitable to increase the basicity of a formulation include lithium hydroxide, sodium hydroxide, potassium hydroxide, sodium carbonate, sodium bicarbonate, sodium phosphate, potassium phosphate, sodium acetate, sodium benzoate, tetrabutylammonium acetate, tetrabutylammonium benzoate, and trialkyl amines. Polyfunctional excipients, such as ethylene diamine tetraacetic acid (EDTA), or a salt thereof, can also be used to modulate acidity or basicity.

A compound disclosed herein can be present in a formulation in any amount. In some embodiments, the compound is present in a concentration of 1 mg/mL to 130 mg/mL, 10 mg/mL to 130 mg/mL, 40 mg/mL to 120 mg/mL, 80 mg/mL to 110 mg/mL, about 1 mg/mL to about 130 mg/mL, about 10 mg/mL to about 130 mg/mL, about 40 mg/mL to about 120 mg/mL, or about 80 mg/mL to about 110 mg/mL. In some embodiments, the compound is present in a concentration of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL. In some embodiments, the compound is present in a concentration of 100 mg/mL. In some embodiments, the compound is present in a concentration of about 100 mg/mL.

A formulation can be prepared by contacting a compound described herein with a solvent or a mixture of solvents. Alternatively, the compound can be contacted with a single solvent, and other solvents can be added subsequently, as a mixture, or sequentially. When the final formulation is a solution, complete solvation can be achieved at whatever step of the process is practical for manufacturing. Optional excipients can be added to the formulation at whatever step is practical for manufacturing.

Preparation of the formulation can be optionally promoted by agitation, heating, or extension of the dissolution period. Non-limiting examples of agitation include shaking, sonication, mixing, stirring, vortex, and combinations thereof.

In some embodiments, a formulation is optionally sterilized. Non-limiting examples of sterilization techniques include filtration, chemical disinfection, irradiation, and heating.

Formulations of the invention are effective for maintaining the therapeutic compound and retarding decomposition during storage and handling, thereby sustaining the efficacy of the compound and the formulation thereof.

One example of storage conditions is to store a formulation of the invention at 2-8° C. for a period of time, for example, a day, a week, a month, 1, 2, 3, 4, 5, 6, 7, 8, 9, 10, 11, or 12 months, about a year, or longer than a year. In some embodiments, the formulation retains about 50%, about 55%, about 60%, about 65%, about 70%, about 75%, about 80%, about 85%, about 90%, about 95%, or about 100% efficacy after storage for 3 months at 2-8° C.

One example of storage conditions is to store a formulation of the invention at 25° C. and 60% relative humidity for a period of time, for example, a day, a week, a month, 1, 2, 3, 4, 5, 6, 7, 8, 9, 10, 11, or 12 months, about a year, or longer than a year. In some embodiments, the formulation retains about 50%, about 55%, about 60%, about 65%, about 70%, about 75%, about 80%, about 85%, about 90%, about 95%, or about 100% efficacy after storage for 3 months at 25° C. and 60% relative humidity.

Dimethyl Sulfoxide (DMSO) for Use According to the Invention

Figure 4:
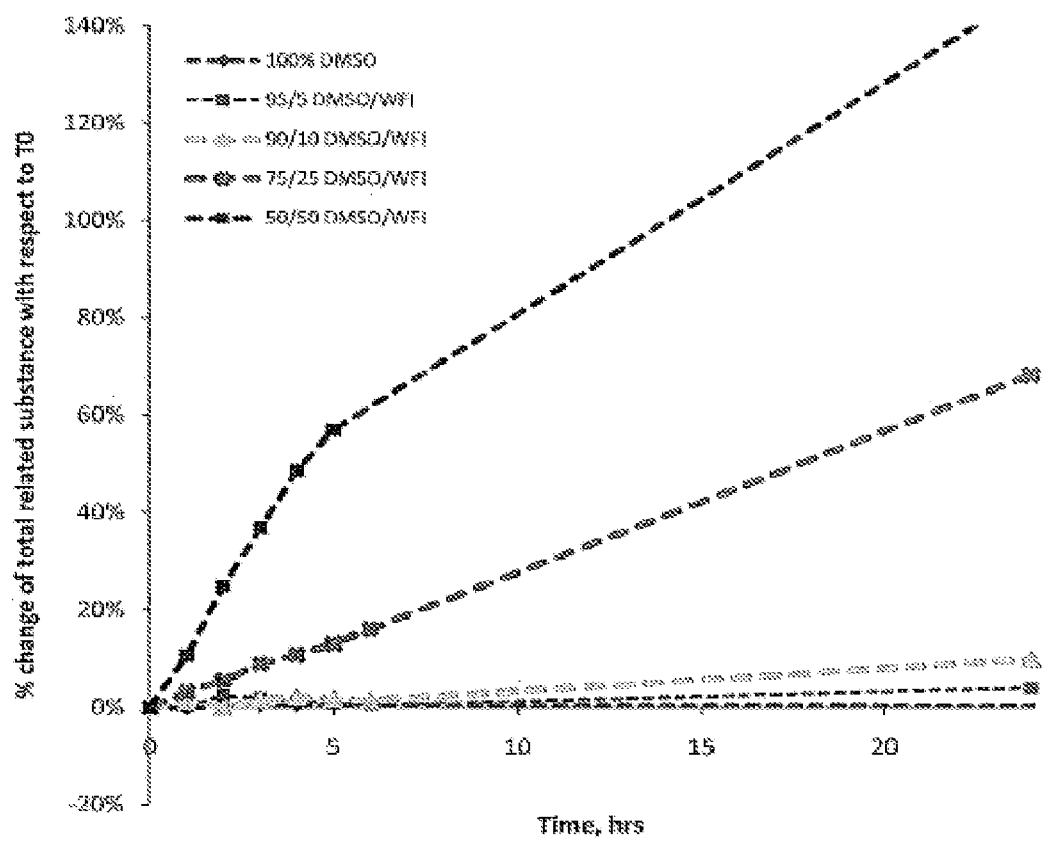
FIG. 4 illustrates the change in total related substances of the sodium salt of a compound of Formula I-1 in various DMSO and DMSO/water compositions.

The use of DMSO as a solvent according to the invention can reduce bulk solution and fill volumes (both bulk and fill volumes can be reduced to ⅕$^{th}$ of those used with aqueous systems) and to remove time and temperature restrictions on scale-up. Moreover, the use of substantially anhydrous DMSO greatly increases stability: increasing water concentration is correlated with a decrease in stability (as shown in FIG. 4, which shows the % change in total related substances of the sodium salt of a compound of Formula I-1 when stored in DMSO or DMSO/water (water for injection, "WFI") at 25° C./60% RH for 24 hours).

Any source of DMSO can be used according to the invention. In some embodiments, the DMSO source is suitable for healthcare and drug delivery applications, for example, conforming to USP or Ph. Eur monographs, or manufactured under cGMP and API guidelines. Grades such as anhydrous, analytical grade, HPLC grade, or Pharma Solvent can be used according to the invention.

In some embodiments, the DMSO for use according to the invention has impurities in low levels, for example <0.2% water by KF, <0.01% non-volatile residue, and/or <0.1% of related compounds.

In some embodiments, the isosteres of DMSO can be used in place of DMSO. In some embodiments, an isostere of DMSO is one in which one or more atom(s) is(are) replaced by a cognate isotope, for example hydrogen by deuterium.

FURTHER EMBODIMENTS

Embodiment 1

A formulation comprising: a) a compound of Formula I or a pharmaceutically-acceptable salt thereof:

(5-azacytosine group)-L-(guanine group)    (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient.

Embodiment 2

The formulation of embodiment 1, wherein L is Formula (II)

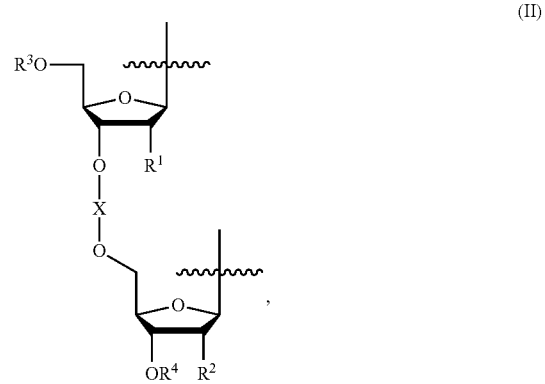

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, a carbonate, or a carbamate; $R^4$ is H, or $R^4$ together with the oxygen atom to which $R^4$ is bound forms an ether, an ester, a carbonate, or a carbamate; and X together with the oxygen atoms to which X is bound forms a phosphodiester, a phosphorothioate diester, a boranophosphate diester, or a methylphosphonate diester.

Embodiment 3

The formulation of embodiment 2, wherein $R^1$ and $R^2$ are independently H, OH, OMe, OEt, OCH$_2$CH$_2$OMe, OBn, or F.

Embodiment 4

The formulation of any one of embodiments 2 and 3, wherein X together with the oxygen atoms to which X is bound forms a phosphodiester.

Embodiment 5

The formulation of any one of embodiments 2-4, wherein $R^1$ and $R^2$ are H.

Embodiment 6

The formulation of any one of embodiments 1-5, wherein the compound of Formula I is any one of I-(1-44).

Embodiment 7

The formulation of any one of embodiments 1-6, wherein the compound of Formula I is:

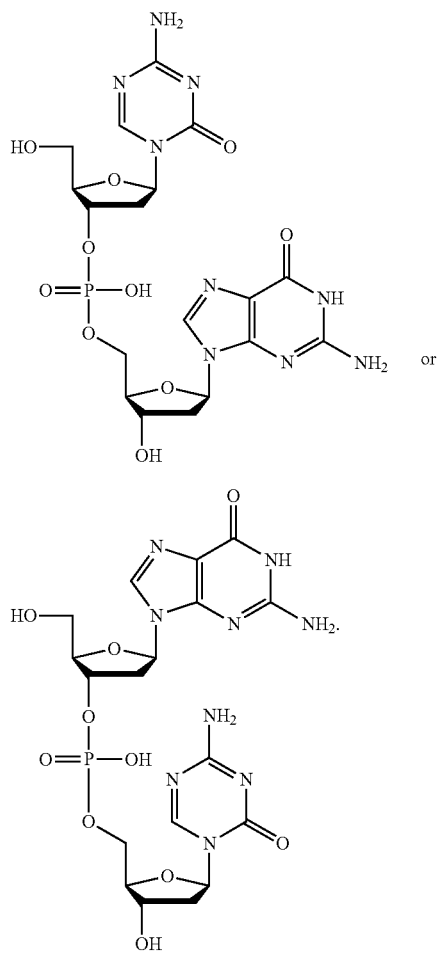

Embodiment 8

The formulation of any one of embodiments 1-7, wherein the solvent comprises: about 65% propylene glycol; about 25% glycerin; and about 10% ethanol.

Embodiment 9

The formulation of any one of embodiments 1-8, wherein the formulation is substantially anhydrous.

Embodiment 10

The formulation of any one of embodiments 1-9, wherein the compound is present in a concentration of about 10 mg/mL to about 130 mg/mL.

Embodiment 11

The formulation of any one of embodiments 1-10, wherein the formulation is a solution.

Embodiment 12

The formulation of any one of embodiments 1-11, wherein the formulation retains about 95% efficacy after storage for 3 months at 2-8° C., or about 68% efficacy after storage for 3 months at 25° C. and 60% relative humidity.

Embodiment 13

A formulation comprising: a) a compound of the formula:

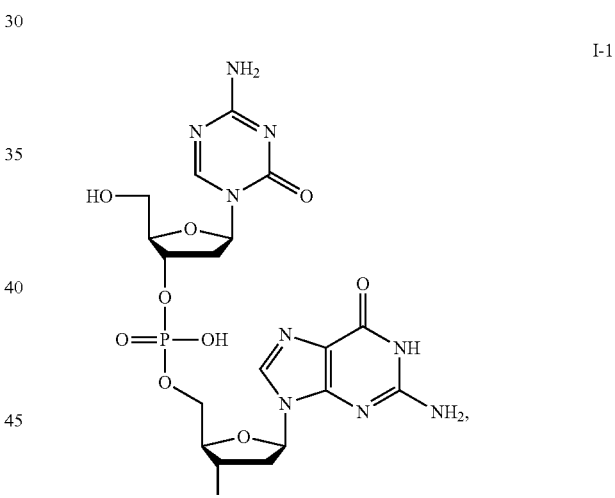

or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

Embodiment 14

The formulation of embodiment 13, wherein the compound exists as a sodium salt.

Embodiment 15

The formulation of any one of embodiments 13 and 14, wherein the solvent is 65% propylene glycol; 25% glycerin; and 10% ethanol.

Embodiment 16

The formulation of any one of embodiments 13-15, wherein the compound is present in a concentration of about 100 mg/mL.

Embodiment 17

A method of treating one or more myelodysplastic syndromes, leukemia, or solid tumours, the method comprising administering a formulation to a subject in need or want thereof, the formulation comprising: a) a therapeutically-effective amount of a compound of Formula I or a pharmaceutically-acceptable salt thereof:

(5-azacytosine group)-L-(guanine group)    (I), wherein L is a phosphorus-containing linker wherein the number of phosphorus atoms in L is 1; b) a solvent comprising: about 45% to about 85% propylene glycol; about 5% to about 45% glycerin; and 0% to about 30% ethanol; and c) optionally, a pharmaceutically-acceptable excipient.

Embodiment 18

The method of embodiment 17, wherein L is Formula (II)

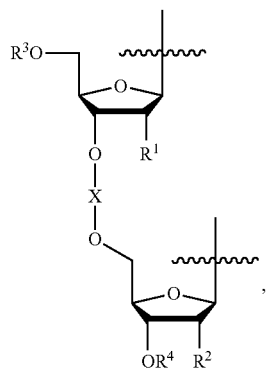

(II)

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, or a carbamate; $R^4$ is H, or $R^4$ together with the oxygen atom to which $R^4$ is bound forms an ether, an ester, or a carbamate; and X together with the oxygen atoms to which X is bound forms a phosphodiester, a phosphorothioate diester, a boranophosphate diester, or a methylphosphonate diester.

Embodiment 19

The method of embodiment 18, wherein $R^1$ and $R^2$ are independently H, OH, OMe, OEt, $OCH_2CH_2OMe$, OBn, or F.

Embodiment 20

The method of any one of embodiments 18 and 19, wherein X together with the oxygen atoms to which X is bound forms a phosphodiester.

Embodiment 21

The method of any one of embodiments 18-20, wherein $R^1$ and $R^2$ are H.

Embodiment 22

The method of any one of embodiments 17-21, wherein the compound of Formula I is any one of I-(1-44).

Embodiment 23

The method of any one of embodiments 17-22, wherein the compound of Formula I is:

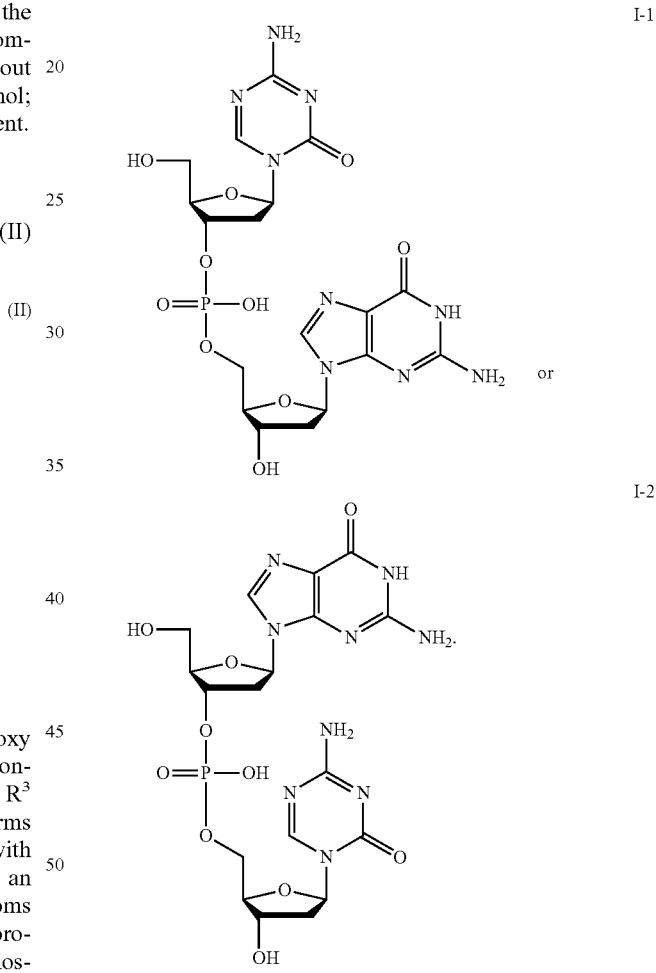

Embodiment 24

The method of any one of embodiments 17-23, wherein the solvent comprises: about 65% propylene glycol; about 25% glycerin; and about 10% ethanol.

Embodiment 25

The method of any one of embodiments 17-24, wherein the formulation is substantially anhydrous.

Embodiment 26

The method of any one of embodiments 17-25, wherein the compound is present in a concentration of about 10 mg/mL to about 130 mg/mL.

Embodiment 27

The method of any one of embodiments 17-26, wherein the formulation is a solution.

Embodiment 28

The method of any one of embodiments 17-27, wherein the myelodysplastic syndrome is acute myeloid leukemia (AML), acute promyelocytic leukemia (APL), acute lymphoblastic leukemia (ALL), or chronic myelogenous leukemia (CML).

Embodiment 29

The method of any one of embodiments 17-28, wherein the administration is subcutaneous.

Embodiment 30

A method of treating one or more myelodysplastic syndromes, leukemia, or solid tumours, the method comprising administering a formulation to a subject in need or want thereof, the formulation comprising: a) a therapeutically-effective amount of a compound of the formula:

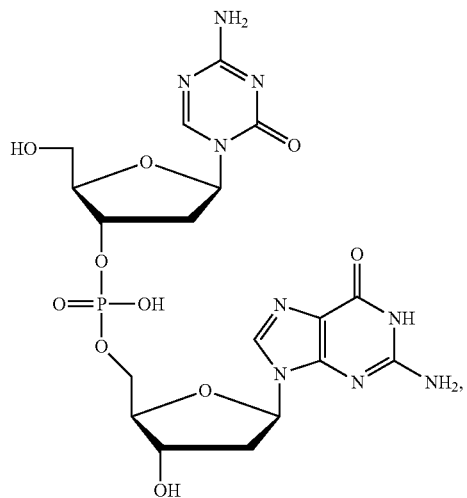

(I-1)

or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

Embodiment 31

The method of embodiment 30, wherein the myelodysplastic syndrome is acute myeloid leukemia (AML), acute promyelocytic leukemia (APL), acute lymphoblastic leukemia (ALL), or chronic myelogenous leukemia (CML).

Embodiment 32

The method of any one of embodiments 30 and 31, wherein the compound exists as a sodium salt.

Embodiment 33

The method of any one of embodiments 30-32, wherein the solvent is 65% propylene glycol; 25% glycerin; and 10% ethanol.

Embodiment 34

The method of any one of embodiments 30-33, wherein the compound is present in a concentration of about 100 mg/mL.

Embodiment 35

The method of any one of embodiments 30-34, wherein the administration is subcutaneous.

Embodiment 36

A use of a compound in the preparation of a medicament for treating one or more myelodysplastic syndromes, leukemia, or solid tumours, the medicament comprising: a) a therapeutically-effective amount of a compound of Formula I or a pharmaceutically-acceptable salt thereof:

(5-azacytosine group)-L-(guanine group)    (I), wherein L is a phosphorus-containing linker wherein the number of phosphorus atoms in L is 1; b) a solvent comprising: about 45% to about 85% propylene glycol; about 5% to about 45% glycerin; and 0% to about 30% ethanol; and c) optionally, a pharmaceutically-acceptable excipient.

Embodiment 37

The use of embodiment 36, wherein L is Formula (II)

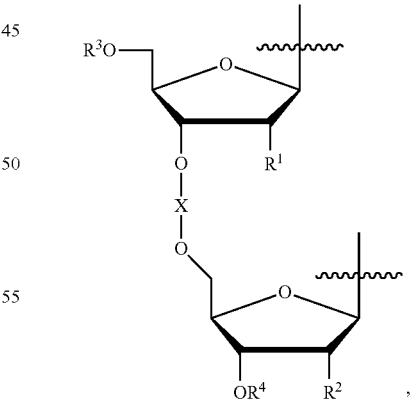

(II)

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, or a carbamate; $R^4$ is H, or $R^4$ together with the oxygen atom to which $R^4$ is bound forms an ether, an ester, or a carbamate; and X together with the oxygen atoms to which X is bound forms a phosphodiester, a phosphorothioate diester, a boranophosphate diester, or a methylphosphonate diester.

Embodiment 38

The use of embodiment 37, wherein $R^1$ and $R^2$ are independently H, OH, OMe, OEt, $OCH_2CH_2OMe$, OBn, or F.

Embodiment 39

The use of any one of embodiments 37 and 38, wherein X together with the oxygen atoms to which X is bound forms a phosphodiester.

Embodiment 40

The use of any one of embodiments 37-39, wherein $R^1$ and $R^2$ are H.

Embodiment 41

The use of any one of embodiments 36-40, wherein the compound of Formula I is any one of I-(1-44).

Embodiment 42

The use of any one of embodiments 36-41, wherein the compound of Formula I is:

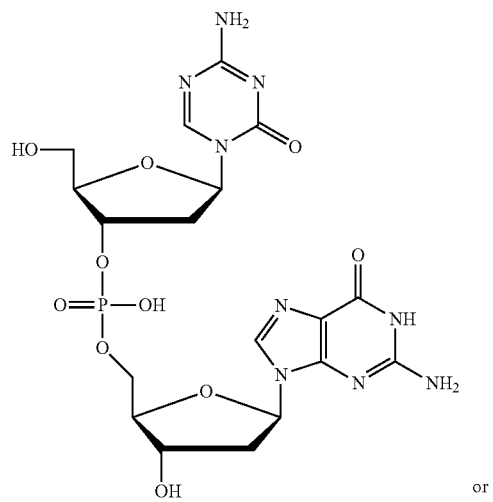

I-1 or

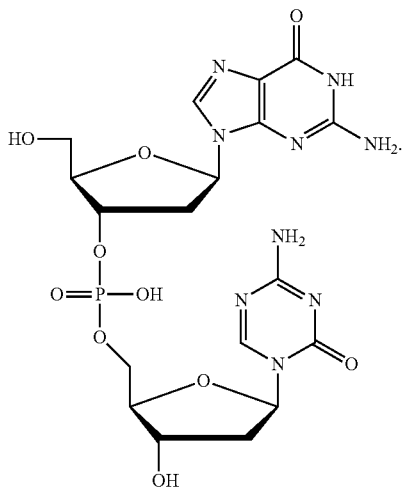

I-2

Embodiment 43

The use of any one of embodiments 36-42, wherein the solvent comprises: about 65% propylene glycol; about 25% glycerin; and about 10% ethanol.

Embodiment 44

The use of any one of embodiments 36-43, wherein the medicament is substantially anhydrous.

Embodiment 45

The use of any one of embodiments 36-44, wherein the compound is present in a concentration of about 10 mg/mL to about 130 mg/mL.

Embodiment 46

The use of any one of embodiments 36-45, wherein the medicament is a solution.

Embodiment 47

The use of any one of embodiments 36-46, wherein the myelodysplastic syndrome is acute myeloid leukemia (AML), acute promyelocytic leukemia (APL), acute lymphoblastic leukemia (ALL), or chronic myelogenous leukemia (CML).

Embodiment 48

The use of any one of embodiments 36-47, wherein the medicament is suitable for subcutaneous administration.

Embodiment 49

A use of a compound in the preparation of a medicament for treating one or more myelodysplastic syndromes, leukemia, or solid tumours, the medicament comprising: a) a therapeutically-effective amount of a compound of the formula:

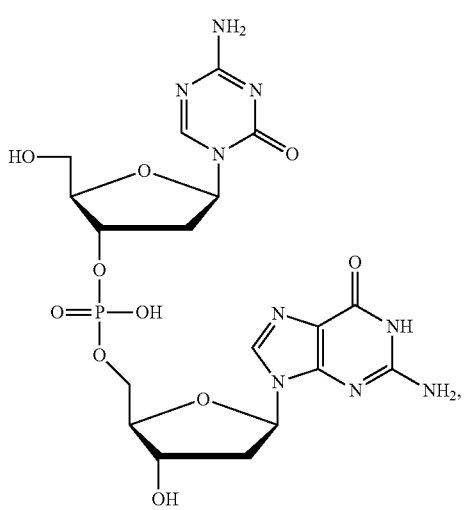

I-1 or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

Embodiment 50

The use of embodiment 49, wherein the myelodysplastic syndrome is acute myeloid leukemia (AML), acute promyelocytic leukemia (APL), acute lymphoblastic leukemia (ALL), or chronic myelogenous leukemia (CML).

Embodiment 51

The use of any one of embodiments 49 and 50, wherein the compound exists as a sodium salt.

Embodiment 52

The use of any one of embodiments 49-51, wherein the solvent is 65% propylene glycol; 25% glycerin; and 10% ethanol.

Embodiment 53

The use of any one of embodiments 49-52, wherein the compound is present in a concentration of about 100 mg/mL.

Embodiment 54

The use of any one of embodiments 49-53, wherein the medicament is suitable for subcutaneous administration.

Embodiment 55

A compound for use in the treatment of one or more myelodysplastic syndromes, leukemia, or solid tumours, the compound comprising: a therapeutically-effective amount of a compound of Formula I or a pharmaceutically-acceptable salt thereof:

(5-azacytosine group)-L-(guanine group)    (I), wherein L is a phosphorus-containing linker wherein the number of phosphorus atoms in L is 1, wherein the compound is provided in a solvent comprising: about 45% to about 85% propylene glycol; about 5% to about 45% glycerin; and 0% to about 30% ethanol, and optionally with a pharmaceutically-acceptable excipient.

Embodiment 56

The compound of embodiment 55, wherein L is Formula (II)

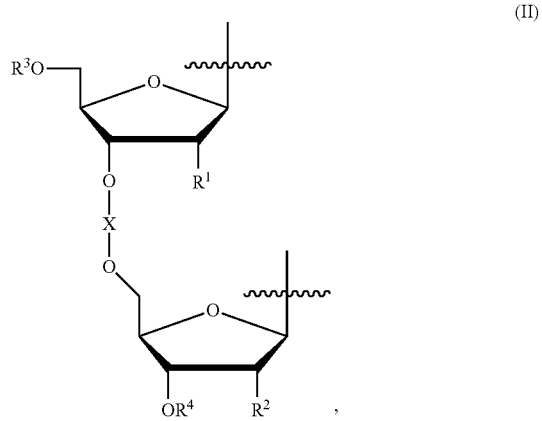

(II)

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, or a carbamate; $R^4$ is H, or $R^4$ together with the oxygen atom to which $R^4$ is bound forms an ether, an ester, or a carbamate; and X together with the oxygen atoms to which X is bound forms a phosphodiester, a phosphorothioate diester, a boranophosphate diester, or a methylphosphonate diester.

Embodiment 57

The compound of embodiment 56, wherein $R^1$ and $R^2$ are independently H, OH, OMe, OEt, $OCH_2CH_2OMe$, OBn, or F.

Embodiment 58

The compound of any one of embodiments 56 and 57, wherein X together with the oxygen atoms to which X is bound forms a phosphodiester.

Embodiment 59

The compound of any one of embodiments 56-58, wherein $R^1$ and $R^2$ are H.

Embodiment 60

The compound of any one of embodiments 55-59, wherein the compound of Formula I is any one of I-(1-44).

Embodiment 61

The compound of any one of embodiments 55-60, wherein the compound of Formula I is:

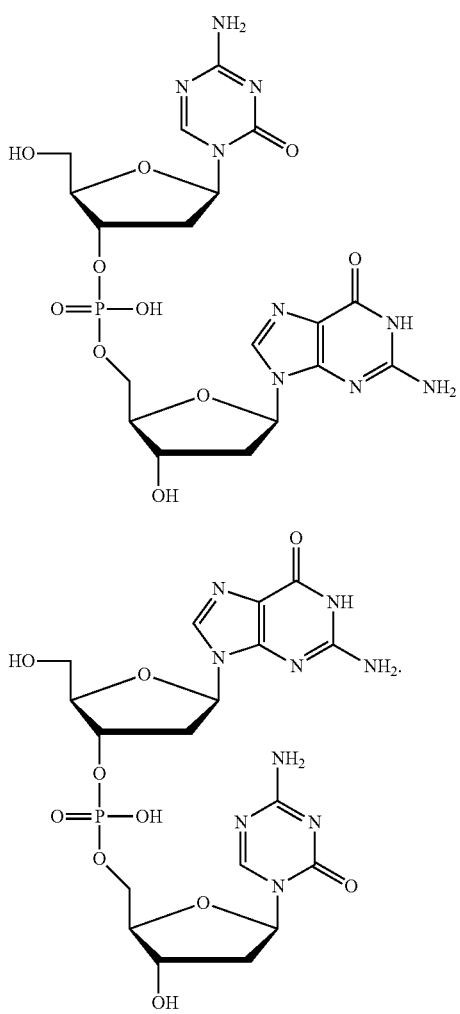

Embodiment 62

The compound of any one of embodiments 55-61, wherein the solvent comprises: about 65% propylene glycol; about 25% glycerin; and about 10% ethanol.

Embodiment 63

The compound of any one of embodiments 55-62, wherein the solvent is substantially anhydrous.

Embodiment 64

The compound of any one of embodiments 55-63, wherein the compound is present in a concentration of about 10 mg/mL to about 130 mg/mL.

Embodiment 65

The compound of any one of embodiments 55-64, wherein the compound forms a solution with the solvent.

Embodiment 66

The compound of any one of embodiments 55-65, wherein the myelodysplastic syndrome is acute myeloid leukemia (AML), acute promyelocytic leukemia (APL), acute lymphoblastic leukemia (ALL), or chronic myelogenous leukemia (CML).

Embodiment 67

The compound of any one of embodiments 55-66, wherein the compound provided in the solvent is suitable for subcutaneous administration.

Embodiment 68

A compound for use in the treatment of one or more myelodysplastic syndromes, leukemia, or solid tumours, the compound having the formula:

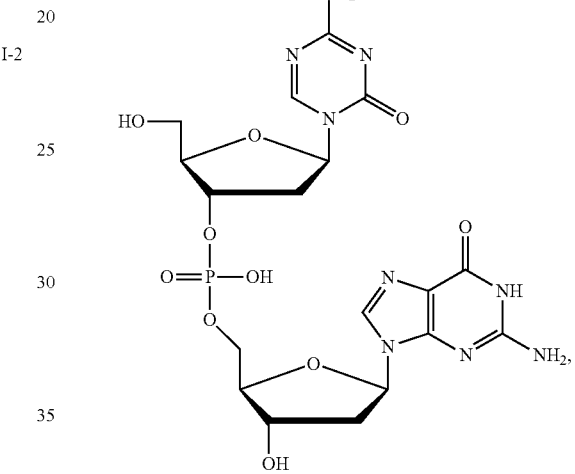

or a pharmaceutically-acceptable salt thereof; wherein the compound is provided in a solvent comprising about 65% propylene glycol; about 25% glycerin; and about 10% ethanol, wherein the solvent is substantially anhydrous, and optionally with a pharmaceutically-acceptable excipient.

Embodiment 69

The compound of embodiment 68, wherein the myelodysplastic syndrome is acute myeloid leukemia (AML), acute promyelocytic leukemia (APL), acute lymphoblastic leukemia (ALL), or chronic myelogenous leukemia (CML).

Embodiment 70

The compound of any one of embodiments 68 and 69, wherein the compound exists as a sodium salt.

Embodiment 71

The compound of any one of embodiments 68-70, wherein the solvent is 65% propylene glycol; 25% glycerin; and 10% ethanol.

Embodiment 72

The compound of any one of embodiments 68-71, wherein the compound is present in a concentration of about 100 mg/mL.

Embodiment 73

The compound of any one of embodiments 68-72, wherein the compound provided in the solvent is suitable for subcutaneous administration.

Dosing and Administration.

Doses of formulations of the invention can be administered to a subject by a method known in the art. Non-limiting examples of methods of administration include subcutaneous injection, intravenous injection, and infusion. In some embodiments, a subject is in need or want of the formulation.

In some embodiments, the invention provides a dosage form comprising: a compound of Formula I or a pharmaceutically-acceptable salt thereof:

(5-azacytosine group)-L-(guanine group)   (I), wherein L is a phosphorus-containing linker wherein the number of phosphorus atoms in L is 1. In some embodiments, the invention provides a dosage form comprising: a) a compound of Formula I or a pharmaceutically-acceptable salt thereof:

(5-azacytosine group)-L-(guanine group)   (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient. Non-limiting examples of compounds suitable for use in dosage forms of the invention include compounds of Formula I wherein L is of Formula II. Non-limiting examples of compounds suitable for use in dosage forms of the invention include compounds I-(1-44).

In some embodiments, the invention provides a method of administering a dosage form comprising: a compound of Formula I or a pharmaceutically-acceptable salt thereof:

(5-azacytosine group)-L-(guanine group)   (I), wherein L is a phosphorus-containing linker wherein the number of phosphorus atoms in L is 1. In some embodiments, the invention provides a method of administering a dosage form comprising: a) a compound of Formula I or a pharmaceutically-acceptable salt thereof:

(5-azacytosine group)-L-(guanine group)   (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient. Non-limiting examples of compounds suitable for administration include compounds of Formula I wherein L is of Formula II. Non-limiting examples of compounds suitable for administration include compounds I-(1-44).

A dose of a formulation contains an amount that is therapeutically-effective for an indication. In some embodiments, a subject is in need or want of therapy for the indication.

A therapeutically-effective amount of a compound of the invention can be expressed as mg of the compound per kg of subject body mass. In some embodiments, a therapeutically-effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, a therapeutically-effective amount is 5 mg/kg, 10 mg/kg, 25 mg/kg, 50 mg/kg, 75 mg/kg, 100 mg/kg, 150 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1,000 mg/kg, about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

In some embodiments, a therapeutically-effective amount can be administered 1-35 times per week, 1-14 times per week, or 1-7 times per week. In some embodiments, a therapeutically-effective amount can be administered 1-10 times per day, 1-5 times per day, 1 time, 2 times, or 3 times per day.

Therapeutic Uses

The pharmaceutical formulations according to the present invention can be used to treat a wide variety of diseases that are sensitive to the treatment with decitabine, including those described herein.

Examples of indications that can be treated using the pharmaceutical formulations of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal gangl-loneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Treatment of abnormal cell proliferation due to insults to body tissue during surgery can be possible for a variety of surgical procedures, including joint surgery, bowel surgery, and cheloid scarring. Diseases that produce fibrotic tissue include emphysema.

Repetitive motion disorders that can be treated using the present invention include carpal tunnel syndrome. An example of cell proliferative disorders that can be treated using the invention is a bone tumor.

The proliferative responses associated with organ transplantation that can be treated using this invention include those proliferative responses contributing to potential organ rejections or associated complications. Specifically, these proliferative responses can occur during transplantation of the heart, lung, liver, kidney, and other body organs or organ systems.

Abnormal angiogenesis that can be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In some embodiments, the pharmaceutical formulations of the present invention can be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases can depend on the severity of the condition, the route of administration, and related factors that can be decided by the attending physician. Generally, accepted and effective daily doses are the amount sufficient to effectively inhibit angiogenesis and/or angiogenic diseases.

Pharmaceutical formulations of the present invention can be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In some embodiments, the pharmaceutical formulations of the present invention can be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present invention can prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but can also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis can actively contribute to, and help maintain, the chronically inflamed state of rheumatoid arthritis. Treatment using the pharmaceutical formulations of the present invention alone or in conjunction with other anti-RA agents can prevent the formation of new blood vessels necessary to maintain the chronic inflammation and provide the RA patient relief from the symptoms.

In some embodiments, the pharmaceutical formulations of the present invention can be used for treating diseases associated with abnormal hemoglobin synthesis. The method comprises administering the pharmaceutical formulations of the present invention to a patient suffering from disease associated with abnormal hemoglobin synthesis. Decitabine containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In some embodiments, the pharmaceutical formulations of the present invention can be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

Gene activation facilitated by the pharmaceutical formulations of the present invention can induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Myelodysplastic syndromes (MDS) are heterogeneous clonal hematopoietic stem cell disorders associated with the presence of dysplastic changes in one or more of the hematopoietic lineages, including dysplastic changes in the myeloid, erythroid, and megakaryocytic series. These changes result in cytopenias in one or more of the three lineages. Subjects afflicted with MDS typically develop complications related to anemia, neutropenia (infections), or thrombocytopenia (bleeding). Generally, from about 10% to about 70% of subjects with MDS develop acute leukemia. Representative myelodysplastic syndromes include acute myeloid leukemia, acute promyelocytic leukemia, acute lymphoblastic leukemia, and chronic myelogenous leukemia.

Acute myeloid leukemia (AML) is the most common type of acute leukemia in adults. Several inherited genetic disorders and immunodeficiency states are associated with an increased risk of AML. These include disorders with defects in DNA stability leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15; 17 chromosomal translocation. This translocation leads to the generation of a fusion transcript comprising a retinoic acid receptor sequence and a promyelocytic leukemia sequence.

Acute lymphoblastic leukemia (ALL) is a heterogeneous disease with distinct clinical features displayed by various subtypes. Reoccurring cytogenetic abnormalities have been demonstrated in ALL. The most common associated cytogenetic abnormality is the 9; 22 translocation leading to development of the Philadelphia chromosome.

Chronic myelogenous leukemia (CML) is a clonal myeloproliferative disorder of a pluripotent stem cell, generally caused by ionizing radiation. CML is characterized by a specific chromosomal abnormality involving the translocation of chromosomes 9 and 22, creating the Philadelphia chromosome.

Compounds described herein and formulations thereof can be used to provide therapy for a MDS. In some embodiments, a compound or formulation thereof can provide therapy for more than one MDS in a single administration. In some embodiments, the invention provides a method of treating one or more myelodysplastic syndromes, leukemia, or solid tumours, the method comprising administering a formulation to a subject in need or want thereof, the formulation comprising a therapeutically-effective amount of a compound of Formula I or a pharmaceutically-acceptable salt thereof:

(5-azacytosine group)-L-(guanine group)　　　(I), wherein L is a phosphorus-containing linker wherein the number of phosphorus atoms in L is 1. In some embodiments, the invention provides a method of treating one or more myelodysplastic syndromes, leukemia, or solid tumours, the method comprising administering a formulation to a subject in need or want thereof, the formulation comprising: a) a therapeutically-effective amount of a compound of Formula I or a pharmaceutically-acceptable salt thereof:

(5-azacytosine group)-L-(guanine group)     (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient. Non-limiting examples of compounds suitable for administration include compounds of Formula I wherein L is of Formula II. Non-limiting examples of compounds suitable for administration include compounds I-(1-44).

In some embodiments, the invention provides a method for treating a myelodysplastic syndrome (MDS). In some embodiments, the invention provides a method for treating one or more myelodysplastic syndromes, leukemia, or solid tumours. In some embodiments, the invention provides a method for treating acute myeloid leukemia (AML). In some embodiments, the invention provides a method for treating acute promyelocytic leukemia (APML) in a subject. In some embodiments, the invention provides a method for treating acute lymphoblastic leukemia (ALL). In some embodiments, the invention provides a method for treating chronic myelogenous leukemia (CML).

In some embodiments, the invention provides a use of a compound in the preparation of a medicament for treating a myelodysplastic syndrome (MDS). In some embodiments, the invention provides a use of a compound in the preparation of a medicament for treating one or more myelodysplastic syndromes, leukemia, or solid tumours. In some embodiments, the invention provides a use of a compound in the preparation of a medicament for treating acute myeloid leukemia (AML). In some embodiments, the invention provides a use of a compound in the preparation of a medicament for treating acute promyelocytic leukemia (APML) in a subject. In some embodiments, the invention provides a use of a compound in the preparation of a medicament for treating acute lymphoblastic leukemia (ALL). In some embodiments, the invention provides a use of a compound in the preparation of a medicament for treating chronic myelogenous leukemia (CML).

In some embodiments, the invention provides a compound for use in treating a myelodysplastic syndrome (MDS). In some embodiments, the invention provides a compound for use in treating one or more myelodysplastic syndromes, leukemia, or solid tumours. In some embodiments, the invention provides a compound for use in treating acute myeloid leukemia (AML). In some embodiments, the invention provides a compound for use in treating acute promyelocytic leukemia (APML) in a subject. In some embodiments, the invention provides a compound for use in treating acute lymphoblastic leukemia (ALL). In some embodiments, the invention provides a compound for use in treating chronic myelogenous leukemia (CML).

In some embodiments, the invention provides a formulation comprising: a) a compound of Formula I or a pharmaceutically-acceptable salt thereof:

(5-azacytosine group)-L-(guanine group)     (I), wherein L is a phosphorus-containing linker wherein the number of phosphorus atoms in L is 1; and b) a solvent comprising: about 45% to about 85% propylene glycol; about 5% to about 45% glycerin; and 0% to about 30% ethanol; and c) optionally, a pharmaceutically-acceptable excipient.

In some embodiments, L is Formula (II)

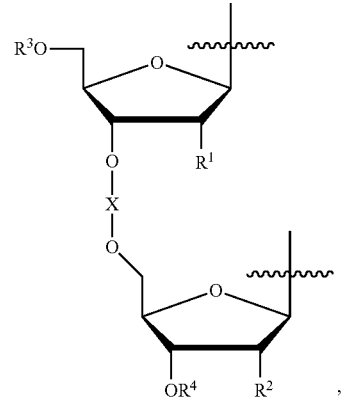

wherein, $R^1$ and $R^2$ are independently H, OH, an alkoxy group, an alkoxyalkoxy group, an acyloxy group, a carbonate group, a carbamate group, or a halogen; $R^3$ is H, or $R^3$ together with the oxygen atom to which $R^3$ is bound forms an ether, an ester, a carbonate, or a carbamate; $R^4$ is H, or $R^4$ together with the oxygen atom to which $R^4$ is bound forms an ether, an ester, a carbonate, or a carbamate; and X together with the oxygen atoms to which X is bound forms a phosphodiester, a phosphorothioate diester, a boranophosphate diester, or a methylphosphonate diester.

In some embodiments, $R^1$ and $R^2$ are independently H, OH, OMe, OEt, $OCH_2CH_2OMe$, OBn, or F.

In some embodiments, X together with the oxygen atoms to which X is bound forms a phosphodiester.

In some embodiments, $R^1$ and $R^2$ are H.

In some embodiments, the compound of Formula I is:

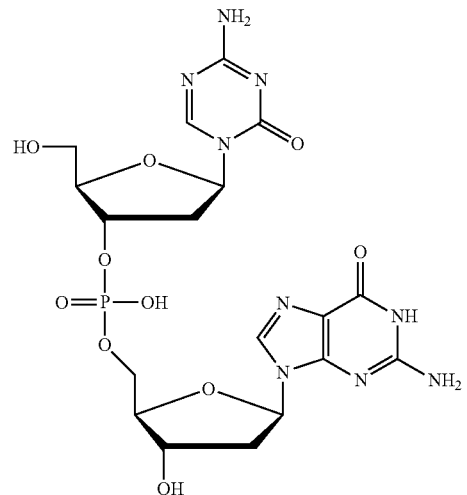

I-1 or

-continued

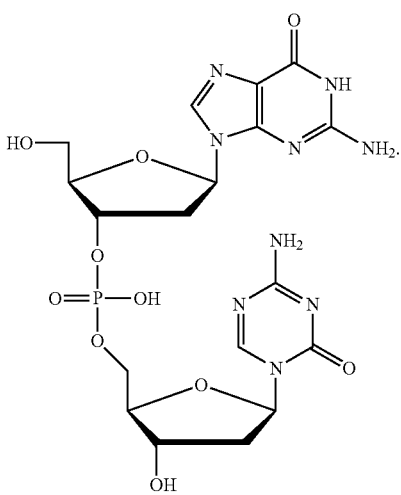

I-2

In some embodiments, the solvent comprises: about 65% propylene glycol; about 25% glycerin; and about 10% ethanol.

In some embodiments, the formulation is substantially anhydrous.

In some embodiments, the compound is present in a concentration of about 10 mg/mL to about 130-150 mg/mL.

In some embodiments, the formulation is a solution.

In some embodiments, the formulation retains about 95% efficacy after storage for 3 months at 2-8° C., or about 68% efficacy after storage for 3 months at 25° C. and 60% relative humidity.

In some embodiments, the invention provides a formulation comprising: a) a compound of the formula:

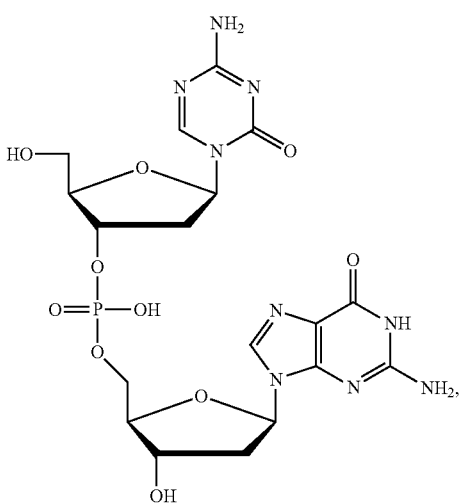

I-1 or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

In some embodiments, the compound exists as a sodium salt.

In some embodiments, the solvent is 65% propylene glycol; 25% glycerin; and 10% ethanol.

In some embodiments, the compound is present in a concentration of about 100 mg/mL.

In some embodiments, the invention provides a method of treating one or more myelodysplastic syndromes, leukemia, or solid tumours, the method comprising administering a formulation to a subject in need or want thereof, the formulation comprising: a) a therapeutically-effective amount of a compound of Formula I or a pharmaceutically-acceptable salt thereof:

(5-azacytosine group)-L-(guanine group)    (I), wherein L is a phosphorus-containing linker wherein the number of phosphorus atoms in L is 1; b) a solvent comprising: about 45% to about 85% propylene glycol; about 5% to about 45% glycerin; and 0% to about 30% ethanol; and c) optionally, a pharmaceutically-acceptable excipient.

In some embodiments, the myelodysplastic syndrome is acute myeloid leukemia (AML), acute promyelocytic leukemia (APL), acute lymphoblastic leukemia (ALL), or chronic myelogenous leukemia (CML).

In some embodiments, the administration is subcutaneous.

In some embodiments, the invention provides a method of treating one or more myelodysplastic syndromes, leukemia, or solid tumours, the method comprising administering a formulation to a subject in need or want thereof, the formulation comprising: a) a therapeutically-effective amount of a compound of the formula:

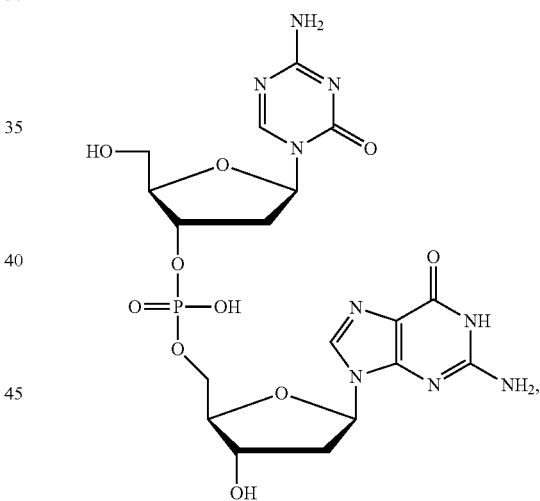

I-1 or a pharmaceutically-acceptable salt thereof; b) a solvent comprising about 65% propylene glycol; about 25% glycerin; and about 10% ethanol, wherein the solvent is substantially anhydrous; and c) optionally, a pharmaceutically-acceptable excipient.

In some embodiments, the myelodysplastic syndrome is acute myeloid leukemia (AML), acute promyelocytic leukemia (APL), acute lymphoblastic leukemia (ALL), or chronic myelogenous leukemia (CML).

EXAMPLES

Example 1: Inhibition of DNA Methylation by Compounds of the Invention

The demethylating activity of compounds of the invention was tested in a cell-based green fluorescent protein (GFP)

assay. In the assay, a decrease in methylation resulting from exposure to a methylation inhibitor led to GFP expression, and was readily scored.

The CMV-EE210 cell line containing the epigenetically silenced GFP transgene was used to assay for reactivation of GFP expression by flow cytometry. CMV-EE210 was made by transfecting NIH 3T3 cells with the pTR-UF/UF1/UF2 plasmid, which contained pBS(+) (Stratagene, Inc.) with a cytomegalovirus (CMV) promoter driving a humanized GFP gene adapted for expression in mammalian cells. After transfection, high-level GFP expressing cells were initially selected by FACS analysis and sorting using a MoFlo cytometer (Cytomation, Inc.).

Decitabine, a potent inhibitor of mammalian DNMT 1, was used as a positive control. To screen for reactivation of CMV-EE210, decitabine (1 µM) or a test compound (30-50 µM) was added to complete medium (phenol red free DMEM (Gibco, Life Technologies) supplemented with 10% fetal bovine serum (Hyclone)). Cells were then seeded to 30% confluence (~5000 cell/well) in a 96-well plate containing the test compounds, and grown for three days in at 37° C. in 5% $CO_2$.

The plates were examined under a fluorescent microscope using a 450-490 excitation filter (13 filter cube, Leica, Deerfield Ill.). Wells were scored g1 positive, g2 positive, or g3 if GFP was expressed in 10%, 30%, >75% of viable cells, respectively.

Table 1 provides the results of the test for decitabine and the test compounds as DNA methylation inhibitors. $GFP_{50}$ is the concentration of an inhibitor at which the Green Fluorescent Protein (GFP) expression level is reduced from g3 to g1/2. Table 1 demonstrates that the tested compounds inhibited DNA methylation effectively at low concentrations, resulting in reactivation of GFP gene transcription.

TABLE 1

| Compound | GFP Expression Level | $GFP_{50}$ (nM) |
|---|---|---|
| Decitabine | g3 | 500 |
| I-1: | g3 | 400 |
| I-2: | g3 | 700 |

Example 2: Stability of a Representative Compound in Solvent Formulations

The stability of a compound of the invention in various formulations under various storage conditions was investigated. Stability was determined by HPLC at the designated time intervals. The results are summarized in Table 2 for formulations comprising a sodium salt of compound I-1:

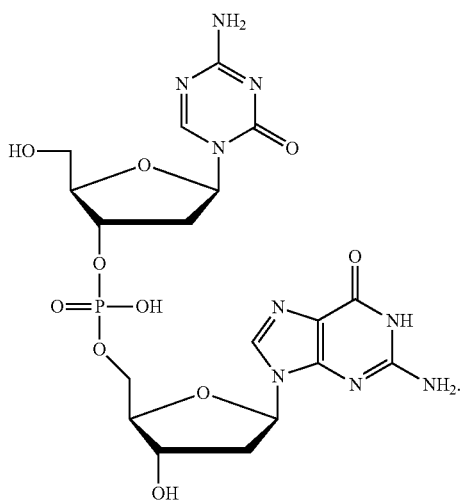

TABLE 2

| Formulation | Storage Conditions | Time Point | Percent compound detected | % decomposition per hour |
|---|---|---|---|---|
| water, pH 7.0 | 2-8° C. | 0 | 95.8% | 0.14 |
| | | 5 hours | 95.1% | |
| water, pH 7.0 | Room temperature | 0 | 95.8% | 1.1 |
| | | 5 hours | 90.4% | |
| DMSO/water (1:1, w/w) | 25° C./60% relative humidity | 0 | 93.7% | 0.72 |
| | | 5 hours | 90.1% | |
| DMSO/water (3:1, w/w) | 25° C./60% relative humidity | 0 | 96.6% | 0.10 |
| | | 24 hours | 94.2% | |
| Propylene glycol/Glycerin (70:30, v/v) | Room temperature | 0 | 96.8% | 0.021 |
| | | 24 hours | 96.3% | |
| Propylene Glycol/ Glycerin/ Ethanol (65:25:10, w/w/w) | 2-8° C. | 0 | 95.8% | 0.00032 |
| | | 3 months | 95.1% | |
| | 25° C./60% relative humidity | 0 | 95.8% | 0.013 |
| | | 3 months | 67.6% | |

Solution of compound I-1 in water at pH 7, the pH at which compounds of this class are most stable, led to rapid decomposition in a few hours, even at lower temperatures. Use of DMSO/water (1:1) gave slightly better results at higher temperatures. An improvement was noted in using 3:1 DMSO/water formulation. The compound was stable in anhydrous DMSO. This stability can facilitate a manufacturing process.

In regard to selection of pharmaceutically acceptable solvents for final formulation ready for administration, the anhydrous propylene glycol/glycerin system provided better stability. The final formulation was prepared by substituting small amounts of propylene glycol and glycerin with ethanol, to provide propylene glycol/glycerin/ethanol (65:25:10). This formulation provided a great improvement in the solubility and stability of the compound at both higher and lower temperatures.

Based on the experiments conducted in water, a 10-fold improvement in stability could have been expected upon changing from room temperature to colder (2-8° C.) storage conditions. However, in the propylene glycol/glycerin/ethanol (65:25:10) system, changing from warmer to colder storage conditions provided a 40-fold improvement in stability. The combined effects of cooling plus the addition of ethanol to the propylene glycol/glycerin system provided a 66-fold improvement in stability. Such great improvements in the stability of compound I-1 during storage could not have been expected.

The propylene glycol/glycerin/ethanol (65:25:10) system provided compound I-1 as a solution, which was smooth, free-flowing, and suitable for passage through a 23-gauge needle without complications or clogging. The maximum solubility of the compound in this medium was determined to be about 130-150 mg/mL, which compares favorably to the aqueous solubility of 20 mg/mL. The good chemical stability taken together with the excellent solubility identified the glycol/glycerin/ethanol (65:25:10) system as a formulation for use in animal experiments.

Example 3: Animal Studies with the Formulation of Example 2

The glycol/glycerin/ethanol (65:25:10) formulation of EXAMPLE 2, containing 100 mg/mL free base equivalent of the sodium salt of compound I-1 was administered to live animals. An analogous decitabine formulation was used for comparison (50 mg lyophilized decitabine powder vial reconstituted to 10 mg/mL with water for injection and administered as infusions by diluting in infusion bags).

Administration of a single dose of the formulations to monkeys (10 mg/kg) produced higher physiological concentrations of compound I-1 ($C_{max}$ 1,130 ng/mL; AUC of 1,469 ng·hr/mL) than of decitabine ($C_{max}$ 160 ng/mL; AUC of 340 ng·hr/mL).

Figure 2:
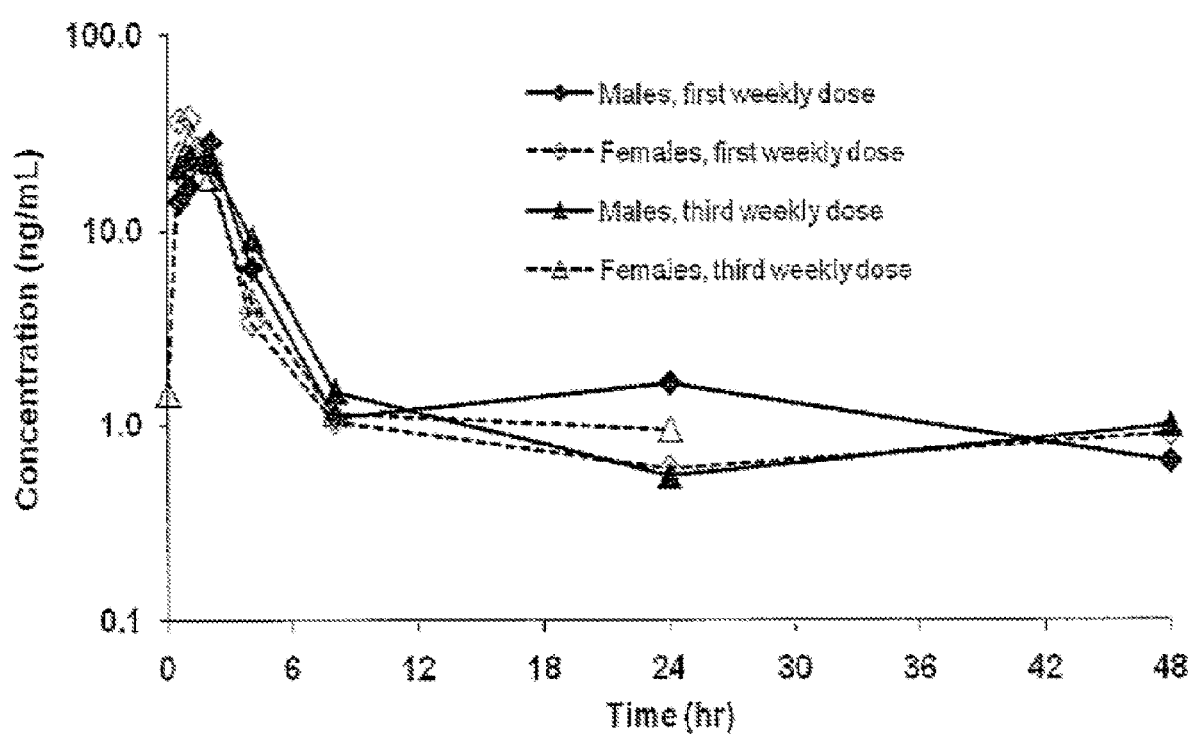
FIG. 2 illustrates the mean plasma concentrations of decitabine in male and female cynomolgus monkeys given weekly subcutaneous doses of decitabine in a pharmacokinetic study.

In a repeat dose study, monkeys were dosed 3× weekly subcutaneously (3 mg/kg). At day 15, the systemic exposure to compound I-1 ($C_{max}$ 181 ng/mL; AUC of 592 ng·hr/mL) was greater than that of decitabine ($C_{max}$ 28 ng/mL; AUC of 99 ng·hr/mL). The pharmacokinetic parameters of the compounds did not vary significantly over the 22-day observation period, and minimal accumulation was detected. (FIGS. 1 and 2.) Pharmacodynamic properties (not shown) were monitored and were acceptable. Blood samples were drawn periodically to assay LINE-1 DNA methylation.

Figure 3:
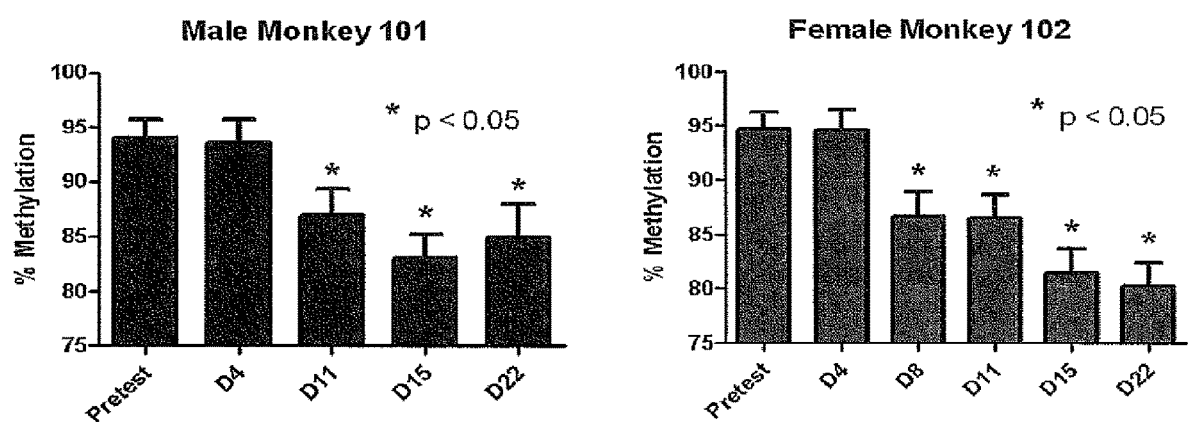
FIG. 3 illustrates the decrease in LINE1 methylation levels observed in blood samples drawn from cynomolgus monkeys on various days (D) after pretest.

Decreases in LINE-1 DNA methylation, the indicator of biological activity, were observed, and the decrease continued until termination of the study on day 22. The observed LINE-1 methylation was significantly different ($p<0.05$) from the methylation level observed prior to initial dosing. (FIG. 3.)

The formulation was well-tolerated in the species tested. Three regimens were evaluated: a) once daily subcutaneous dose in rats and rabbits for 5 days; b) once weekly subcutaneous dose in rabbits and cynomolgus monkeys for 28 days as tolerated; and c) twice weekly subcutaneous dose in rats for 28 days as tolerated. Rabbits tolerated the 5-day regimen well, up to a dose of 1.5 mg/kg/day, which is equivalent to 18 mg/kg/day in humans, and the weekly regimen up to a dose of 1.5 mg/kg/week for 3 weeks.

Cynomolgus monkeys tolerated the weekly regimen well, up to a dose of 3.0 mg/kg/week for 3 weeks, which is equivalent to 36 mg/kg/week. Rats tolerated much higher doses: 30 mg/kg/day over 5 days; and 20 mg/kg twice weekly for 4 weeks.

The main toxicity in all experiments was myelosuppression. However, the subcutaneous formulation tested exhibited less myelosuppression and faster recovery.

Example 4: Preparation of a Kit According to the Invention

First Vessel: Compound of Formula I-1 for Injection, 100 mg

The sodium salt of the compound of the formula:

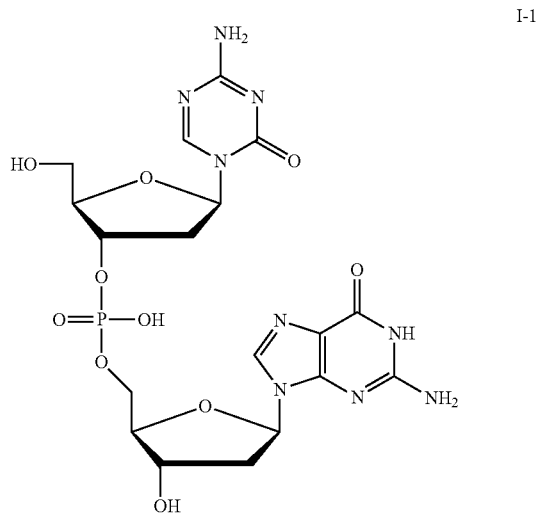

I-1 was prepared as described in U.S. Pat. No. 7,700,567 (the content of which is hereby incorporated by reference) by coupling is (where $R_1$=carbamate protective group) with phosphoramidite building block id:

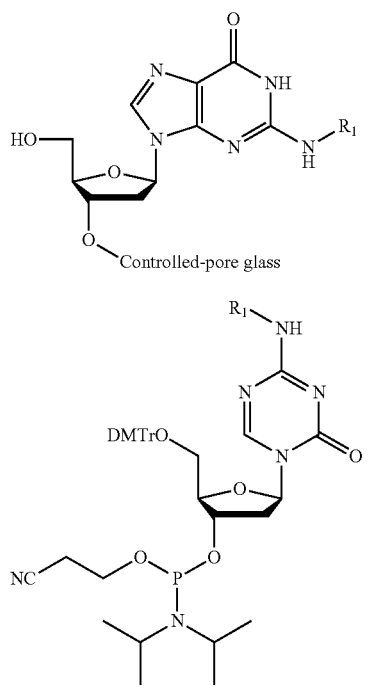

1s

1d

A protected 2'-deoxyguanosine-linked CPG solid support Is (where $R_1$=tert-butyl phenoxyacetyl) was coupled with 2-2.5 equivalents of phenoxyacetyl decitabine phosphoramidite (Id, where $R_1$=phenoxyacetyl) in the presence of 60% of 0.3 M benzylthiotetrazole activator (in acetonitrile) for 10 minutes. The CPG solid support containing protected DpG dinucleotide was treated with 20 mL of 50 mM $K_2CO_3$ in methanol for 1 hour and 20 minutes. The coupled product was oxidized, the protective group was removed, and the resultant compound was washed, filtered, and purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes.

The ESI-MS (-ve) of DpG dinucleotide 2b:

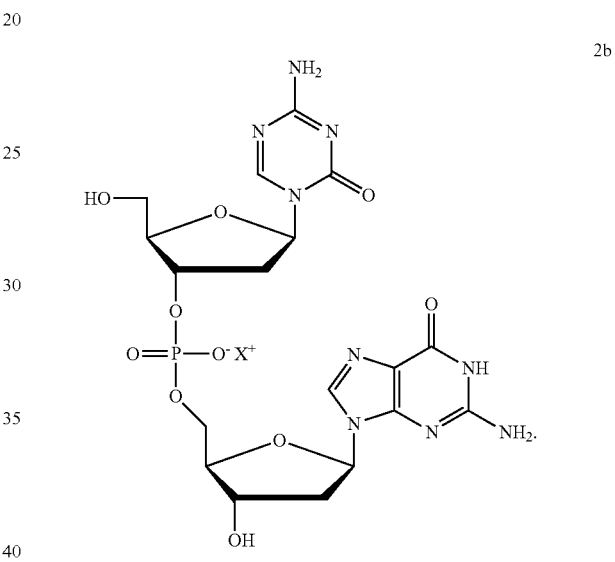

2b where $X^+$=triethylammonium (calculated exact mass for the neutral compound $C_{18}H_{24}N_9O_{10}P$ is 557.14), exhibited m/z 556.1 [M-H]$^-$ and 1113.1 for [2M-H]$^-$ (see mass spectrum in FIG. 31 of U.S. Pat. No. 7,700,567).

The sodium salt of the compound of formula I-1, i.e. DpG dinucleotide 2b, where $X^1$=sodium, was obtained by re-dissolving the triethylammonium salt in 4 mL water, 0.2 mL 2M $NaClO_4$ solution. When 36 mL acetone was added, the dinucleotide precipitated. The solution was kept at -20° C. for several hours and centrifugated at 4000 rpm for 20 minutes. The supernatant was discarded and the solid was washed with 30 mL acetone followed by an additional centrifugation at 4000 rpm for 20 minutes. The precipitate, which was dissolved in water and freeze dried, exhibited m/z 556.0 [M-H]$^-$ (see mass spectrum in FIG. 36 of U.S. Pat. No. 7,700,567).

Compounding and Filling of Bulk Formulation

1. Based on the assay value of the lot of the sodium salt of the compound of formula I-1, needed quantities the salt and DMSO were calculated and weighed appropriately for the intended batch scale.

2. The sodium salt of the compound of formula I-1 was dissolved in DMSO utilizing an overhead mixer in an appropriately sized stainless steel (SS) vessel.

3. Upon complete solubilization of the drug in DMSO, samples of the bulk solution were tested using a UV or HPLC in-process method to determine that the amount of the sodium salt of the compound of formula I-1 was within 95-105% of the target concentration.

4. Bulk solution was filtered through a series of two pre-sterilized 0.2 micron sterilizing filters that were DMSO compatible, and collected into a 2 L SS surge vessel.

5. Filtration rate was continuously adjusted by visual monitoring of quantity available for filling in the surge vessel.

6. One gram of the filtered bulk solution was filled into each of the 5 cc depyrogenated, clear glass vials and the operation was continued with until all of the filtered bulk solution was filled.

7. Each vial was automatically and partially stoppered on the fill line with a fluoropolymer coated, chlorobutyl rubber lyo stopper that was pre-sterilized.

8. Product vials were transferred to lyophilizer under aseptic transfer conditions for initiation of lyophilization cycle.

Lyophilization and Capping of Vials

1. Vials were lyophilized using the cycle parameters as below.

| | | Primary/Secondary Drying Temperature | | | | Final Set point (stoppering conditions) |
|---|---|---|---|---|---|---|
| | −40° C. | −5° C. | 10° C. | 30° C. | 60° C. | 25° C. |
| Freezing | | | | | | |
| Ramp time (min) | 133 | 117 | 50 | 67 | 100 | — |
| Time (min.) | 360 | 1440 | 1440 | 1440 | 1440 | hold |
| Vacuum (mTorr) | — (note: 100 mT for evacuation at −50° C.) | 100 | 100 | 50 | 50 | 50 mT before back fill |

2. Upon completion of the lyophilization cycle, the lyophilizer was back filled with nitrogen, and the vials were completely and automatically stoppered.

3. Vials were aseptically transferred to an isolator where each of the vials was automatically capped with a blue aluminum flip-off cap.

4. Vials were visually inspected before proceeding with sampling for release testing, and the labeling and packaging operation. Vials were kept at 2-8° C. until ready.

Labeling and Packaging

Each vial was labeled per approved content, and packaged individually into a heat-sealed aluminum foil pouch with a desiccant under vacuum. The foil pouch was labeled outside with the same label as was used for the product vial. Labeled and packaged vials were stored at 2-8° C. until further distribution.

Residual DMSO

Four batches of the same scale of 3000 vials/batch were prepared using the same process as described above. DMSO was consistently removed to the following residual levels to yield a solid white powder, demonstrating that lyophilization of the sodium salt of the compound of formula I-1 out of DMSO as described above yielded a safe and chemically stable sodium salt of the compound of formula I-1 as a powder:

| # | DMSO in mg/vial |
|---|---|
| Batch 1 | 25 |
| Batch 2 | 28 |
| Batch 3 | 27 |
| Batch 4 | 29 |

Second Vessel: Diluent for Reconstitution of the Sodium Salt of the Compound of Formula I-1, 3 mL Compounding and Filling of Bulk Formulation 1. Calculated quantities (see table below) of propylene glycol, ethanol, and glycerin in the aforementioned order were added into an appropriately sized stainless steel vessel equipped with an overhead mixer.

| | % of each ingredient | Grade | Function |
|---|---|---|---|
| Propylene glycol | 65 | NF, PhEur | Solvent |
| Glycerin | 25 | NF, PhEur | Solvent |
| Alcohol/Ethanol | 10 | USP, PhEur | Thinning agent |

2. Intermittent mixing during addition of components was followed by at least 30 minutes of mixing to yield a well-mixed solution.

3. Bulk solution was filtered through a series of two pre-sterilized 0.2 micron compatible sterilizing filters, and collected into a 2 L SS surge vessel.

4. Filtration rate was adjusted by visual monitoring of quantity available for filling in the surge vessel.

5. At least 3.15 g, equivalent to 3.0 mL, of the filtered bulk solution was filled into each of the 5 cc depyrogenated, clear glass vials followed by automatic stoppering using fluoropolymer coated chlorobutyl rubber closures.

6. Stoppered vials were capped with sterilized white aluminum flip-off caps.

7. Vials were visually inspected prior to sampling for the release testing and labeling operation and were stored at 2-30° C. until ready.

Labeling and Packaging

Each diluent vial was labeled per approved content. Labeled vials were stored at 2-30° C. until further distribution.

What is claimed is:

1. A method comprising:
   a) dissolving a compound in a substantially anhydrous solution to form a formulation, wherein the substantially anhydrous solution comprises:
      i) about 65% propylene glycol (w/w);
      ii) about 25% glycerin (w/w); and
      iii) about 10% ethanol (w/w) of the formulation; and
   b) storing the formulation for a day.

2. The method of claim 1, further comprising storing the formulation for a week.

3. The method of claim 1, further comprising storing the formulation for 1-12 months.

4. The method of claim 1, wherein the formulation is stored at a temperature of 2° C. to 30° C.

5. The method of claim 1, wherein the formulation is stored at a temperature of 2° C. to 6° C.

6. The method of claim 1, wherein the formulation is stored at a temperature of 25° C.

7. The method of claim 1, wherein the compound is a compound of Formula I:

(5-azacytosine group)-L-(guanine group)    (I), wherein L is a phosphorus-containing linker wherein the number of phosphorus atoms in L is 1, or a pharmaceutically-acceptable salt thereof.

8. The method of claim 1, wherein the compound is present in the formulation at a concentration of 1 mg/mL to 130 mg/mL.

9. The method of claim 1, wherein the compound is present in the formulation at a concentration of 80 mg/mL to 110 mg/mL.

10. The method of claim 7, wherein the compound is a compound of the formula:

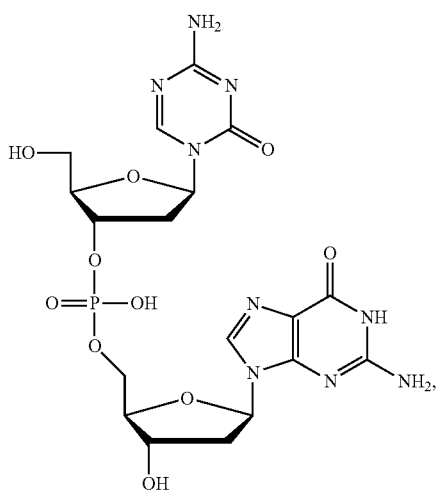

or a pharmaceutically acceptable salt thereof.

11. The method of claim 10, wherein the pharmaceutically acceptable salt is a sodium salt.

12. The method of claim 1, wherein the formulation retains about 65% efficacy after storage for 3 months at 25° C. and 60% relative humidity.

13. The method of claim 1, further comprising, after (b), administering a therapeutically effective amount of the formulation to a subject in need thereof, wherein the administering treats a condition in the subject.

14. The method of claim 13, wherein the administering inhibits DNA methylation in the subject.

15. The method of claim 13, wherein the condition is a myelodysplastic syndrome.

16. The method of claim 13, wherein the condition is leukemia.

17. The method of claim 13, wherein the administration is subcutaneous administration.

18. The method of claim 1, wherein the formulation further comprises dimethyl sulfoxide (DMSO).

19. The method of claim 18, wherein DMSO is present in the formulation in an amount of up to about 200% w/w when compared to an amount of the compound present in the formulation.

* * * * *